US009353354B2

(12) United States Patent
Leblanc et al.

(10) Patent No.: US 9,353,354 B2
(45) Date of Patent: May 31, 2016

(54) BACTERIAL IODOPEROXIDASES FROM ZOBELLIA GALACTANIVORANS, METHODS OF PREPARATION AND USES THEREOF

(75) Inventors: Catherine Leblanc, Plougonven (FR); Ludovic Delage, Mespaul (FR); Gurvan Michel, Roscoff (FR); Etienne Rebuffet, Roscoff (FR); Mirjam Czjzek, Plougoulm (FR); Philippe Potin, Roscoff (FR)

(73) Assignee: Centre National de la Recherche Scientifique (FR)

( * ) Notice: Subject to any disclaimer, the term of this patent is extended or adjusted under 35 U.S.C. 154(b) by 0 days.

(21) Appl. No.: 14/130,546

(22) PCT Filed: Jul. 5, 2012

(86) PCT No.: PCT/EP2012/063144
§ 371 (c)(1),
(2), (4) Date: Jan. 2, 2014

(87) PCT Pub. No.: WO2013/004783
PCT Pub. Date: Jan. 10, 2013

(65) Prior Publication Data
US 2014/0212931 A1    Jul. 31, 2014

(30) Foreign Application Priority Data
Jul. 5, 2011  (EP) ..................... 11305864

(51) Int. Cl.
*C12N 9/08* (2006.01)
*C02F 3/34* (2006.01)
*C12P 9/00* (2006.01)

(52) U.S. Cl.
CPC .............. *C12N 9/0065* (2013.01); *C02F 3/342* (2013.01); *C12P 9/00* (2013.01); *C12Y 111/01008* (2013.01)

(58) Field of Classification Search
None
See application file for complete search history.

(56) References Cited

FOREIGN PATENT DOCUMENTS

WO    0200838 A1    3/2002
WO    2004078976 A1    9/2004

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Altschul, S.F., et al., "Basic Local Alignment Search Tool", J Mol Biol, May 15, 1990, pp. 403-410, vol. 215, No. 3.
Altschul, S.F., et al., "Gapped BLAST and PSI-BLAST: a new generation of protein database search programs", Nucleic Acids Research., Jul. 16, 1997, pp. 3389-3402, vol. 25, No. 17, Oxford University Press.

Barbeyon, T., et al., "Zobellia galactanovorans gen. nov., sp. nov., a marine species of Flavobacteriaceae isolated from a red alga, and classification of [Cytophaga] uliginosa (ZoBell and Upham 1944) Reichenbach 1989 as Zobellia uliginosa gen. nov., comb. nov.", International Journal of Systematic Evolutionary Microbiology., 2001, pp. 985-997, vol. 51, Great Britain.
Butler, A., et al., Vanadium in Proteins and Enzymes, Handbook on Metalloproteins (bertini, I., Sigel, A., and Sigel, H. eds),2001, pp. 153-179, Marcel Dekker, Inc., New York, Basel.
Carter, J.N., et al., "Reactivity of recombinant and mutant vanadium bromoperoxidase from the red alga Corallina officinalis", Journal of Inorganic Biochemistry 2005, pp. 59-69, vol. 91, Department of Chemistry and Biochemistry, University California Santa Barbara, Santa Barbara, CA, USA.
Colin, C., et al., "Vanadium-dependent iodoperoxidases in Laminaria digitata, a novel biochemical function diverging from brown algal bromoperoxidases", J Biol. Inorg. Chem, 2005, pp. 156-166, vol. 10, Online at SBIC.
Groisillier, A., et al., "Marine-Express: taking advantage of high throughput cloning and expression strategies for the post-genomic analysis of marine organisms", Cell Factories, 2010, vol. 9, No. 45.
Isupov, M. N., et al., "Crystal Structure of Dodecameric Vanadiumdependent Bromoperoxidase from the Red Algae Corallina officinalis", J. Mol. Biol. 2000, pp. 1035-1049, vol. 299, Academic Press.
Jordan P., et al., Native bromoperoxideases do not bind to nitrocellulose: Use of DEAE-cellulose as an alternative in blotting, Electrophoresis, 1990, pp. 653-655, vol. 11, No. 8, Weinheim, Germany.
La Barre, S., et al., "The Halogenated Metabolism of Brown Algae (Phaeophyta), Its Biological Importance and Its Environmental Significance", Drugs, Mar. 2010, pp., 988-1010. vol. 8, No. 4, Roscoff, France.
Messerschmidt, A., et al., "X-ray structure of a vanadium-containing enzyme: Chloroperoxidase from the fungus Curvularia inaequalis", Proceedings of the National Academy of Sciences of the U.S.. 1996, pp. 392-396, vol. 93, Max Planck Institute of Biochemistry, Martinsried, Germany; and tE. C. Slater Institute, Department of Biochemistry, University of Amsterdam, Amsterdam, The Netherlands.
Needleman, et al., "A General Method Applicable to the Search for Similarities in the Amino Acid Sequence of Two Proteins", J. Mol. Biol., 1970, pp. 443-453, vol. 48, No. 3, Department of Biochemistry, Northeastern, and Nuclear Medicine Service, V.A. Research Hospital, Chicago, IL, U.S.A.
Nielsen, H., et al., "Machine learning approaches for the prediction of signal peptides and other protein sorting signals", Protein Engineering, pp. 3-9, vol. 12, No. 1, Center for Biological Sequence Analysis Department of Biotechnology, The Technical University of Denmark, Lyngby, Denmark and Department of Biochemistry, Arrhenius Laboratory, Stockholm University, Stockholm, Sweden.

(Continued)

Primary Examiner — Christian Fronda
(74) Attorney, Agent, or Firm — Banner & Witcoff, Ltd.

(57) ABSTRACT

The present invention concerns iodoperoxidases from Zobellia galactanivorans, isolated nucleic acids encoding same, as well as methods for preparing these enzymes. Moreover, the invention is also directed to the use of such iodoperoxidases in a wide range of industrial, pharmaceutical, medical, cosmetics, and ecological applications, as well as in the food industry.

7 Claims, 5 Drawing Sheets

(56) References Cited

OTHER PUBLICATIONS

Figure 1:
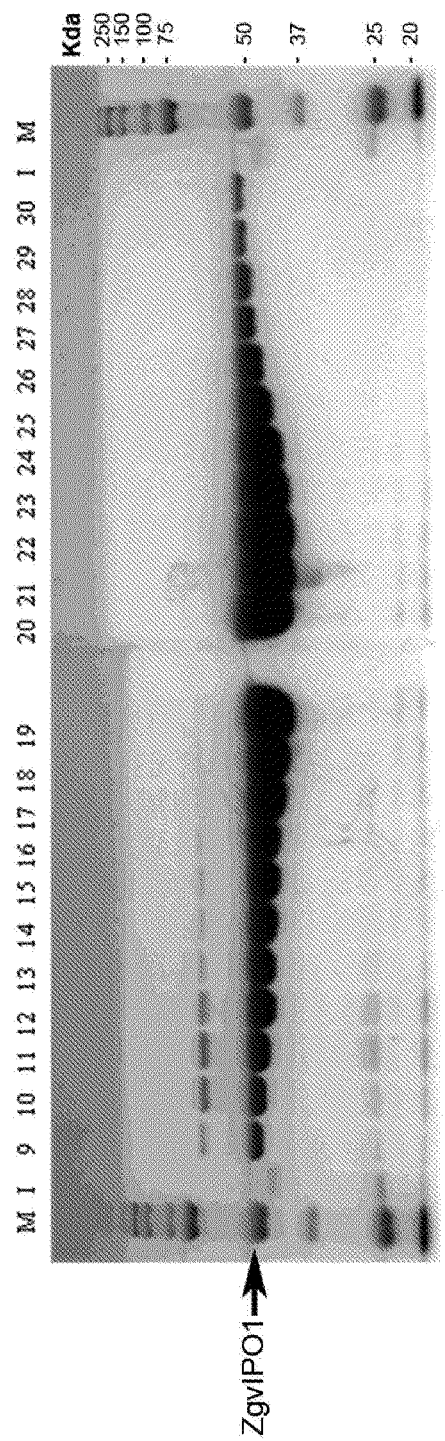

Ohshiro, T., et al., "Expression of the vanadium-dependent bromoperoxidase gene from a marine macro-alga Corallina pilulifera in *Saccharomyces cerevisiae* and characterization of the recombinant enzyme", Phytochemistry, 2002, pp. 595-601, vol. 60, Department of Biotechnology, Tottori University, Tottori, Japan, Institute for Molecular Chemistry, University of Amsterdam, Amsterdam, The Netherlands.

Pearson et al., "Improved tools for biological sequence comparison", Proc. Natl. Acad. Sci. USA, 1988, pp. 2444-2448, vol. 95, No. 5, Department of Biochemistry, University of Virginia, Charlottesville, VA 22908; and Mathematical Research Branch, National Institute of Diabetes and Digestive and Kidney Diseases, National Institutes of Health, Bethesda, MD.

Shimonishi, M., et al., "Cloning and expression of the gene for a vanadium-dependent bromoperoxidase from a marine macro-alga, Corallina pilulifera", FEBS letters, 2001, pp. 105-110, vol. 428, Federation of European Biochemical Societies.

Smith et al., "Overlapping Genes and Information Theory", J. Theor. Biol., 1981, pp. 370-380, vol. 91, No. 2, Academic Press Inc., London.

Studier, "Protein production by auto-induction in high-density shaking cultures", Protein Expr Purif, 2005, pp. 207-234, vol. 41, Biology Department, Brookhaven National Laboratory, Upton, NY, USA.

Verhaeghe, E., et al., "A colorimetric assay for steady-state analyses of iodo- and bromoperoxidase activities", Analytical Biochemistry, 2008, pp. 60-65, Vol. 379, No. 1, Elsevier Inc.

Vilter, H.,"Vanadium and its role in Life", Metal ions in biological systems (Sigel, H., and Sigel, A., eds), 1995, pp. 325-362, vol. 31, Marcel Dekker, Inc. New York, Basel, Hong Kong.

Vreeland, V., et al., Direct Submission, Sep. 12, 1998, Environmental Science, Policy and Management, University of California, 2 pages.

Vreeland, V., et al., "Fucus, Vanadium Peroxidase: Minimum Catalytic Domain Size Retaining Peroxidase Activity", Journal of Phycology, Dec. 2000, vol. 36, Issue Supplement 53, pp. 69-70.

Weyand, M., et al., "X-ray Structure Determination of a Vanadiumdependent Haloperoxidase from Ascophyllum nodosum at 2.0 AÊ Resolution", J Mol Biol. 1999, pp. 595-611, vol. 293, No. 3, Academic Press.

Zobell, C., Studies on Marine Bacteria. The Cultural Requirements of Heterotrophic Aerobes, J. Marine Research., 1941, pp. 42-75, vol. 4, Scripps Institution of Oceanography, University of California, La Jolla, California.

Rebuffet, E., "These de doctorat de l'universite Pierre et Marie Curie—Etude structurale et fonctionnelle de glycoside hydrolases et d'une iodo-peroxydase de la flavobacterie marine Zobellia galactanivorans, impliquees dans l'interaction avec les algues", Oct. 18, 2011 pp. 1-203.

International Search Report regarding International Application No. PCT/EP2012/063144 dated Sep. 19, 2012.

\* cited by examiner

SEQUENCE LISTING

```
<160> NUMBER OF SEQ ID NOS: 16

<210> SEQ ID NO 1
<211> LENGTH: 433
<212> TYPE: PRT
<213> ORGANISM: artificial
<220> FEATURE:
<223> OTHER INFORMATION: ZgvIPO1 amino-acid sequence A

<400> SEQUENCE: 1

Lys Ala Pro Gln Lys Glu Glu Pro Ile Asn Ile Thr Pro Glu Glu Leu
1               5                   10                  15

Asp Ala Ser Ile Asp Arg Val Thr Glu Ile Met Ile His Asp Ile Phe
            20                  25                  30

Ser Pro Pro Val Ala Ser Arg Ile Phe Ala Tyr Pro Asn Val Ala Ala
        35                  40                  45

Tyr Glu Ile Val Ala Ala Thr Asn Asp Asn Tyr Asn Ser Leu Ala Gly
    50                  55                  60

Gln Leu Asn Gly Leu Thr Ala Ile Pro Glu Pro Asp Thr Thr Lys Thr
65                  70                  75                  80

Ile Asn Tyr Glu Leu Ala Ala Val Val Ala His Met Glu Leu Ser Lys
                85                  90                  95

Arg Leu Ile Phe Ser Glu Asp Arg Met Glu Ser Leu Arg Asp Ser Leu
            100                 105                 110

Tyr Met Val Trp Glu Gly Lys Asn Pro Val Leu Phe Ser Asp Ser Lys
        115                 120                 125

Ala Tyr Gly Leu Gln Val Ala Asp His Ile Gly Glu Trp Met Asn Lys
    130                 135                 140

Asp Asn Tyr Ala Gln Thr Arg Thr Met Pro Lys Phe Thr Val Asp Ala
145                 150                 155                 160

Asp Asp Pro Gly Arg Trp Gln Pro Thr Pro Ala Tyr Met Asp Gly
                165                 170                 175

Ile Glu Pro His Trp Asn Lys Ile Arg Pro Phe Val Leu Asp Ser Ala
            180                 185                 190
```

Ala Gln Phe Lys Pro Val Pro Pro Ala Tyr Ser Leu Glu Glu Asp
        195                 200                 205

Ser Ala Phe Tyr Lys Glu Leu Lys Glu Val Tyr Asp Val Arg Asn Lys
    210                 215                 220

Ile Thr Glu Glu Gly Asp Ser Ser Glu Ile Gln Ile Ala Arg Phe
225                 230                 235                 240

Trp Asp Cys Asn Pro Tyr Val Ser Val Thr Arg Gly His Leu Met Phe
                245                 250                 255

Ala Thr Lys Lys Ile Thr Pro Gly Ala His Trp Met Gly Ile Ala Lys
        260                 265                 270

Ile Ala Ala Arg Lys Thr Asn Ser Asp Phe Ala Lys Thr Leu Phe Ala
        275                 280                 285

Tyr Thr Lys Ala Ser Val Ala Met Ala Asp Ala Phe Ile Ser Cys Trp
        290                 295                 300

Asp Glu Lys Tyr Arg Ser Asn Leu Ile Arg Pro Glu Thr Val Ile Asn
305                 310                 315                 320

Gln His Ile Asp Asp Ser Trp Lys Pro Val Leu Gln Thr Pro Pro Phe
                325                 330                 335

Pro Glu Tyr Thr Ser Gly His Ser Val Val Ser Gly Ala Ala Ser Val
                340                 345                 350

Val Leu Thr Glu Val Phe Gly Asp Asn Phe Ser Phe Asp Asp Thr
        355                 360                 365

Glu Val Pro Tyr Gly Leu Pro Ile Arg Ser Phe Lys Ser Phe Lys Gln
        370                 375                 380

Ala Ala Asp Glu Ala Ala Ile Ser Arg Met Tyr Gly Gly Ile His Tyr
385                 390                 395                 400

Arg Ala Ala Ile Glu Val Gly Val Lys Gln Gly Arg Asp Leu Gly Thr
                405                 410                 415

Phe Val Val Asn Lys Leu His Met Leu Ser Asp Lys Lys Val Ala Gln
                420                 425                 430

Asn

<210> SEQ ID NO 2
<211> LENGTH: 428
<212> TYPE: PRT
<213> ORGANISM: artificial
<220> FEATURE:
<223> OTHER INFORMATION: ZgvIPO1 amino-acid sequence B

<400> SEQUENCE: 2

Glu Glu Pro Ile Asn Ile Thr Pro Glu Glu Leu Asp Ala Ser Ile Asp
1               5                   10                  15

Arg Val Thr Glu Ile Met Ile His Asp Ile Phe Ser Pro Pro Val Ala
            20                  25                  30

Ser Arg Ile Phe Ala Tyr Pro Asn Val Ala Ala Tyr Glu Ile Val Ala
        35                  40                  45

Ala Thr Asn Asp Asn Tyr Asn Ser Leu Ala Gly Gln Leu Asn Gly Leu
    50                  55                  60

Thr Ala Ile Pro Glu Pro Asp Thr Thr Lys Thr Ile Asn Tyr Glu Leu
65                  70                  75                  80

Ala Ala Val Val Ala His Met Glu Leu Ser Lys Arg Leu Ile Phe Ser
                85                  90                  95

Glu Asp Arg Met Glu Ser Leu Arg Asp Ser Leu Tyr Met Val Trp Glu
            100                 105                 110

```
Gly Lys Asn Pro Val Leu Phe Ser Asp Ser Lys Ala Tyr Gly Leu Gln
            115                 120                 125

Val Ala Asp His Ile Gly Glu Trp Met Asn Lys Asp Asn Tyr Ala Gln
        130                 135                 140

Thr Arg Thr Met Pro Lys Phe Thr Val Asp Ala Asp Pro Gly Arg
145                 150                 155                 160

Trp Gln Pro Thr Pro Ala Tyr Met Asp Gly Ile Glu Pro His Trp
                165                 170                 175

Asn Lys Ile Arg Pro Phe Val Leu Ser Ala Ala Gln Phe Lys Pro
            180                 185                 190

Val Pro Pro Ala Tyr Ser Leu Glu Glu Asp Ser Ala Phe Tyr Lys
        195                 200                 205

Glu Leu Lys Glu Val Tyr Asp Val Arg Asn Lys Ile Thr Glu Gly
    210                 215                 220

Asp Ser Ser Glu Glu Ile Gln Ile Ala Arg Phe Trp Asp Cys Asn Pro
225                 230                 235                 240

Tyr Val Ser Val Thr Arg Gly His Leu Met Phe Ala Thr Lys Lys Ile
                245                 250                 255

Thr Pro Gly Ala His Trp Met Gly Ile Ala Lys Ile Ala Ala Arg Lys
            260                 265                 270

Thr Asn Ser Asp Phe Ala Lys Thr Leu Phe Ala Tyr Thr Lys Ala Ser
        275                 280                 285

Val Ala Met Ala Asp Ala Phe Ile Ser Cys Trp Asp Glu Lys Tyr Arg
    290                 295                 300

Ser Asn Leu Ile Arg Pro Glu Thr Val Ile Asn Gln His Ile Asp Asp
305                 310                 315                 320

Ser Trp Lys Pro Val Leu Gln Thr Pro Pro Phe Pro Glu Tyr Thr Ser
                325                 330                 335

Gly His Ser Val Val Ser Gly Ala Ala Ser Val Val Leu Thr Glu Val
            340                 345                 350

Phe Gly Asp Asn Phe Ser Phe Asp Asp Thr Glu Val Pro Tyr Gly
        355                 360                 365

Leu Pro Ile Arg Ser Phe Lys Ser Phe Lys Gln Ala Ala Asp Glu Ala
370                 375                 380

Ala Ile Ser Arg Met Tyr Gly Gly Ile His Tyr Arg Ala Ala Ile Glu
385                 390                 395                 400

Val Gly Val Lys Gln Gly Arg Asp Leu Gly Thr Phe Val Val Asn Lys
                405                 410                 415

Leu His Met Leu Ser Asp Lys Lys Val Ala Gln Asn
            420                 425

<210> SEQ ID NO 3
<211> LENGTH: 450
<212> TYPE: PRT
<213> ORGANISM: Zobellia galactanivorans
<220> FEATURE:
<221> NAME/KEY: misc_feature
<223> OTHER INFORMATION: ZgvIPO1 amino-acid sequence with the putative
      native peptide signal sequence (wild-type ZgvIPO1)

<400> SEQUENCE: 3

Met Lys Lys Ile Leu Ile Ala Leu Ile Ser Phe Ala Phe Ala Val Ser
1               5                   10                  15

Cys Lys Ala Pro Gln Lys Glu Glu Pro Ile Asn Ile Thr Pro Glu Glu
            20                  25                  30

Leu Asp Ala Ser Ile Asp Arg Val Thr Glu Ile Met Ile His Asp Ile
```

```
                35                  40                  45
Phe Ser Pro Pro Val Ala Ser Arg Ile Phe Ala Tyr Pro Asn Val Ala
 50                  55                  60
Ala Tyr Glu Ile Val Ala Ala Thr Asn Asp Asn Tyr Asn Ser Leu Ala
 65                  70                  75                  80
Gly Gln Leu Asn Gly Leu Thr Ala Ile Pro Glu Pro Asp Thr Thr Lys
                 85                  90                  95
Thr Ile Asn Tyr Glu Leu Ala Ala Val Val Ala His Met Glu Leu Ser
                100                 105                 110
Lys Arg Leu Ile Phe Ser Glu Asp Arg Met Glu Ser Leu Arg Asp Ser
                115                 120                 125
Leu Tyr Met Val Trp Glu Gly Lys Asn Pro Val Leu Phe Ser Asp Ser
                130                 135                 140
Lys Ala Tyr Gly Leu Gln Val Ala Asp His Ile Gly Glu Trp Met Asn
145                 150                 155                 160
Lys Asp Asn Tyr Ala Gln Thr Arg Thr Met Pro Lys Phe Thr Val Asp
                165                 170                 175
Ala Asp Asp Pro Gly Arg Trp Gln Pro Thr Pro Pro Ala Tyr Met Asp
                180                 185                 190
Gly Ile Glu Pro His Trp Asn Lys Ile Arg Pro Phe Val Leu Asp Ser
                195                 200                 205
Ala Ala Gln Phe Lys Pro Val Pro Pro Ala Tyr Ser Leu Glu Glu
                210                 215                 220
Asp Ser Ala Phe Tyr Lys Glu Leu Lys Glu Val Tyr Asp Val Arg Asn
225                 230                 235                 240
Lys Ile Thr Glu Glu Gly Asp Ser Ser Glu Glu Ile Gln Ile Ala Arg
                245                 250                 255
Phe Trp Asp Cys Asn Pro Tyr Val Ser Val Thr Arg Gly His Leu Met
                260                 265                 270
Phe Ala Thr Lys Lys Ile Thr Pro Gly Ala His Trp Met Gly Ile Ala
                275                 280                 285
Lys Ile Ala Ala Arg Lys Thr Asn Ser Asp Phe Ala Lys Thr Leu Phe
                290                 295                 300
Ala Tyr Thr Lys Ala Ser Val Ala Met Ala Asp Ala Phe Ile Ser Cys
305                 310                 315                 320
Trp Asp Glu Lys Tyr Arg Ser Asn Leu Ile Arg Pro Glu Thr Val Ile
                325                 330                 335
Asn Gln His Ile Asp Asp Ser Trp Lys Pro Val Leu Gln Thr Pro Pro
                340                 345                 350
Phe Pro Glu Tyr Thr Ser Gly His Ser Val Val Ser Gly Ala Ala Ser
                355                 360                 365
Val Val Leu Thr Glu Val Phe Gly Asp Asn Phe Ser Phe Asp Asp Asp
                370                 375                 380
Thr Glu Val Pro Tyr Gly Leu Pro Ile Arg Ser Phe Lys Ser Phe Lys
385                 390                 395                 400
Gln Ala Ala Asp Glu Ala Ala Ile Ser Arg Met Tyr Gly Gly Ile His
                405                 410                 415
Tyr Arg Ala Ala Ile Glu Val Gly Val Lys Gly Arg Asp Leu Gly
                420                 425                 430
Thr Phe Val Val Asn Lys Leu His Met Leu Ser Asp Lys Lys Val Ala
                435                 440                 445
Gln Asn
450
```

<210> SEQ ID NO 4
<211> LENGTH: 445
<212> TYPE: PRT
<213> ORGANISM: artificial
<220> FEATURE:
<223> OTHER INFORMATION: ZgvIPO1 amino-acid sequence A with a histidine tag sequence

<400> SEQUENCE: 4

```
Met Gly Ser Ser His His His His His Gly Ser Lys Ala Pro Gln
1               5                   10                  15

Lys Glu Glu Pro Ile Asn Ile Thr Pro Glu Glu Leu Asp Ala Ser Ile
            20                  25                  30

Asp Arg Val Thr Glu Ile Met Ile His Asp Ile Phe Ser Pro Pro Val
            35                  40                  45

Ala Ser Arg Ile Phe Ala Tyr Pro Asn Val Ala Ala Tyr Glu Ile Val
        50                  55                  60

Ala Ala Thr Asn Asp Asn Tyr Asn Ser Leu Ala Gly Gln Leu Asn Gly
65                  70                  75                  80

Leu Thr Ala Ile Pro Glu Pro Asp Thr Thr Lys Thr Ile Asn Tyr Glu
                85                  90                  95

Leu Ala Ala Val Val Ala His Met Glu Leu Ser Lys Arg Leu Ile Phe
            100                 105                 110

Ser Glu Asp Arg Met Glu Ser Leu Arg Asp Ser Leu Tyr Met Val Trp
            115                 120                 125

Glu Gly Lys Asn Pro Val Leu Phe Ser Asp Ser Lys Ala Tyr Gly Leu
130                 135                 140

Gln Val Ala Asp His Ile Gly Glu Trp Met Asn Lys Asp Asn Tyr Ala
145                 150                 155                 160

Gln Thr Arg Thr Met Pro Lys Phe Thr Val Asp Ala Asp Pro Gly
                165                 170                 175

Arg Trp Gln Pro Thr Pro Pro Ala Tyr Met Asp Gly Ile Glu Pro His
            180                 185                 190

Trp Asn Lys Ile Arg Pro Phe Val Leu Asp Ser Ala Ala Gln Phe Lys
            195                 200                 205

Pro Val Pro Pro Ala Tyr Ser Leu Glu Glu Asp Ser Ala Phe Tyr
210                 215                 220

Lys Glu Leu Lys Glu Val Tyr Asp Val Arg Asn Lys Ile Thr Glu Glu
225                 230                 235                 240

Gly Asp Ser Ser Glu Glu Ile Gln Ile Ala Arg Phe Trp Asp Cys Asn
                245                 250                 255

Pro Tyr Val Ser Val Thr Arg Gly His Leu Met Phe Ala Thr Lys Lys
            260                 265                 270

Ile Thr Pro Gly Ala His Trp Met Gly Ile Ala Lys Ile Ala Ala Arg
            275                 280                 285

Lys Thr Asn Ser Asp Phe Ala Lys Thr Leu Phe Ala Tyr Thr Lys Ala
        290                 295                 300

Ser Val Ala Met Ala Asp Ala Phe Ile Ser Cys Trp Asp Glu Lys Tyr
305                 310                 315                 320

Arg Ser Asn Leu Ile Arg Pro Glu Thr Val Ile Asn Gln His Ile Asp
                325                 330                 335

Asp Ser Trp Lys Pro Val Leu Gln Thr Pro Pro Phe Pro Glu Tyr Thr
            340                 345                 350

Ser Gly His Ser Val Val Ser Gly Ala Ala Ser Val Val Leu Thr Glu
```

-continued

```
        355                 360                 365

Val Phe Gly Asp Asn Phe Ser Phe Asp Asp Asp Thr Glu Val Pro Tyr
    370                 375                 380

Gly Leu Pro Ile Arg Ser Phe Lys Ser Phe Lys Gln Ala Ala Asp Glu
385                 390                 395                 400

Ala Ala Ile Ser Arg Met Tyr Gly Gly Ile His Tyr Arg Ala Ala Ile
                405                 410                 415

Glu Val Gly Val Lys Gln Gly Arg Asp Leu Gly Thr Phe Val Val Asn
            420                 425                 430

Lys Leu His Met Leu Ser Asp Lys Lys Val Ala Gln Asn
        435                 440                 445

<210> SEQ ID NO 5
<211> LENGTH: 440
<212> TYPE: PRT
<213> ORGANISM: artificial
<220> FEATURE:
<223> OTHER INFORMATION: ZgvIPO1 amino-acid sequence B with a histidine
      tag sequence

<400> SEQUENCE: 5

Met Gly Ser Ser His His His His His His Gly Ser Glu Glu Pro Ile
1               5                   10                  15

Asn Ile Thr Pro Glu Glu Leu Asp Ala Ser Ile Asp Arg Val Thr Glu
            20                  25                  30

Ile Met Ile His Asp Ile Phe Ser Pro Pro Val Ala Ser Arg Ile Phe
        35                  40                  45

Ala Tyr Pro Asn Val Ala Ala Tyr Glu Ile Val Ala Ala Thr Asn Asp
    50                  55                  60

Asn Tyr Asn Ser Leu Ala Gly Gln Leu Asn Gly Leu Thr Ala Ile Pro
65                  70                  75                  80

Glu Pro Asp Thr Thr Lys Thr Ile Asn Tyr Glu Leu Ala Ala Val Val
                85                  90                  95

Ala His Met Glu Leu Ser Lys Arg Leu Ile Phe Ser Glu Asp Arg Met
            100                 105                 110

Glu Ser Leu Arg Asp Ser Leu Tyr Met Val Trp Glu Gly Lys Asn Pro
        115                 120                 125

Val Leu Phe Ser Asp Ser Lys Ala Tyr Gly Leu Gln Val Ala Asp His
    130                 135                 140

Ile Gly Glu Trp Met Asn Lys Asp Asn Tyr Ala Gln Thr Arg Thr Met
145                 150                 155                 160

Pro Lys Phe Thr Val Asp Ala Asp Asp Pro Gly Arg Trp Gln Pro Thr
                165                 170                 175

Pro Pro Ala Tyr Met Asp Gly Ile Glu Pro His Trp Asn Lys Ile Arg
            180                 185                 190

Pro Phe Val Leu Asp Ser Ala Ala Gln Phe Lys Pro Val Pro Pro Pro
        195                 200                 205

Ala Tyr Ser Leu Glu Glu Asp Ser Ala Phe Tyr Lys Glu Leu Lys Glu
    210                 215                 220

Val Tyr Asp Val Arg Asn Lys Ile Thr Glu Glu Gly Asp Ser Ser Glu
225                 230                 235                 240

Glu Ile Gln Ile Ala Arg Phe Trp Asp Cys Asn Pro Tyr Val Ser Val
                245                 250                 255

Thr Arg Gly His Leu Met Phe Ala Thr Lys Lys Ile Thr Pro Gly Ala
            260                 265                 270
```

```
His Trp Met Gly Ile Ala Lys Ile Ala Ala Arg Lys Thr Asn Ser Asp
            275                 280                 285

Phe Ala Lys Thr Leu Phe Ala Tyr Thr Lys Ala Ser Val Ala Met Ala
            290                 295                 300

Asp Ala Phe Ile Ser Cys Trp Asp Glu Lys Tyr Arg Ser Asn Leu Ile
305                 310                 315                 320

Arg Pro Glu Thr Val Ile Asn Gln His Ile Asp Asp Ser Trp Lys Pro
            325                 330                 335

Val Leu Gln Thr Pro Pro Phe Pro Glu Tyr Thr Ser Gly His Ser Val
            340                 345                 350

Val Ser Gly Ala Ala Ser Val Val Leu Thr Glu Val Phe Gly Asp Asn
            355                 360                 365

Phe Ser Phe Asp Asp Asp Thr Glu Val Pro Tyr Gly Leu Pro Ile Arg
            370                 375                 380

Ser Phe Lys Ser Phe Lys Gln Ala Ala Asp Glu Ala Ala Ile Ser Arg
385                 390                 395                 400

Met Tyr Gly Gly Ile His Tyr Arg Ala Ala Ile Glu Val Gly Val Lys
            405                 410                 415

Gln Gly Arg Asp Leu Gly Thr Phe Val Val Asn Lys Leu His Met Leu
            420                 425                 430

Ser Asp Lys Lys Val Ala Gln Asn
            435                 440

<210> SEQ ID NO 6
<211> LENGTH: 22
<212> TYPE: PRT
<213> ORGANISM: artificial
<220> FEATURE:
<223> OTHER INFORMATION: amino-acid sequence of the putative native
      signal peptide sequence of the wild-type ZgvIPO1

<400> SEQUENCE: 6

Met Lys Lys Ile Leu Ile Ala Leu Ile Ser Phe Ala Phe Ala Val Ser
1               5                   10                  15

Cys Lys Ala Pro Gln Lys
            20

<210> SEQ ID NO 7
<211> LENGTH: 66
<212> TYPE: DNA
<213> ORGANISM: artificial
<220> FEATURE:
<223> OTHER INFORMATION: nucleotide sequence of the putative native
      signal peptide sequence of the wild type ZgvIPO1

<400> SEQUENCE: 7
atgaagaaga ttcttatcgc actaatatcg tttgcttttg cggtttcgtg caaagctcca      60
caaaaa                                                                66

<210> SEQ ID NO 8
<211> LENGTH: 12
<212> TYPE: PRT
<213> ORGANISM: artificial
<220> FEATURE:
<223> OTHER INFORMATION: amino-acid sequence of a histidine tag

<400> SEQUENCE: 8

Met Gly Ser Ser His His His His His His Gly Ser
1               5                   10
```

```
<210> SEQ ID NO 9
<211> LENGTH: 36
<212> TYPE: DNA
<213> ORGANISM: artificial
<220> FEATURE:
<223> OTHER INFORMATION: nucleotide sequence of a histidine tag

<400> SEQUENCE: 9
atgggcagca gccaccatca ccatcaccat ggatcc                                36

<210> SEQ ID NO 10
<211> LENGTH: 1299
<212> TYPE: DNA
<213> ORGANISM: artificial
<220> FEATURE:
<223> OTHER INFORMATION: ZgvIPO1 nucleotide sequence A

<400> SEQUENCE: 10
aaagctccac aaaaagaaga acctattaac attaccccg  aagagcttga cgcttcaata      60
gacagggtga cggaaattat gatccacgat atcttttccc ctcccgttgc gagtaggatc     120
tttgcctatc ccaacgttgc cgcctacgaa attgtagccg ccaccaatga caactacaac     180
tccttggccg ccaattgaa  cgggctgacc gccataccgg aacccgatac cactaagacc     240
atcaactacg agcttgcagc cgtcgtcgcc catatggagc ttagcaaaag gttgattttc     300
tcagaagacc gaatggaatc cctgcgcgat agcctataca tggtttggga agggaaaaat     360
cctgttctat tctccgattc caaagcctac ggcctacaag tggccgacca tataggcgaa     420
tggatgaaca aggacaatta cgcccaaacc cgcaccatgc cgaaatttac ggtagatgcg     480
gacgaccccg ccgctggca  acccacccca cctgcctaca tggacggtat tgaacccca      540 tggaataaaa tcaggccatt tgtattggat tcggcagcac agttcaagcc cgttccacct     600
ccggcatatt cccttgaaga agactccgcg ttttataaag aattaaaaga agtctatgac     660
gtaaggaaca aaatcaccga ggaaggcgat agttccgaag aaattcagat tgcccgcttt     720
tgggattgta acccttatgt atcggttacc cgtggccact tgatgttcgc caccaagaaa     780
ataaccccag gtgcgcattg gatgggaatt gccaaaattg ccgcacgtaa aaccaacagt     840
gattttgcca aaacccttttt cgcctatacc aaggcctcgg tagccatggc ggatgccttt     900
atcagttgtt gggacgaaaa gtacagaagc aacctcatcc gtccggaaac cgtaatcaac     960
caacatatag acgacagctg gaaaccagtg ctacaaaccc ctccgttttcc agagtacacc    1020 agcggacata gtgtagtctc aggggcggca tcggttgtac tgaccgaggt ctttggtgac    1080
aatttctcct tgacgacga  tacgaagta  ccttacggcc tacctatccg aagctttaaa    1140
tcctttaagc aagctgccga cgaagcagcg atcagtcgca tgtacggagg catacactac    1200
cgtgcagcta ttgaagtagg ggtaaaacaa ggcagggacc taggtacctt tgtcgtaaac    1260
aaactacata tgctatccga taagaaagta gcccaaaac                           1299

<210> SEQ ID NO 11
<211> LENGTH: 1284
<212> TYPE: DNA
<213> ORGANISM: artificial
<220> FEATURE:
<223> OTHER INFORMATION: ZgvIPO1 nucleotide sequence B

<400> SEQUENCE: 11
gaagaaccta ttaacattac ccccgaagag cttgacgctt caatagacag ggtgacggaa      60
attatgatcc acgatatctt ttcccctccc gttgcgagta ggatctttgc ctatcccaac     120
```

```
gttgccgcct acgaaattgt agccgccacc aatgacaact acaactcctt ggccggccaa    180
ttgaacgggc tgaccgccat accggaaccc gataccacta agaccatcaa ctacgagctt    240
gcagccgtcg tcgcccatat ggagcttagc aaaaggttga ttttctcaga agaccgaatg    300
gaatccctgc gcgatagcct atacatggtt tgggaaggga aaaatcctgt tctattctcc    360
gattccaaag cctacggcct acaagtggcc gaccatatag gcgaatggat gaacaaggac    420
aattacgccc aaacccgcac catgccgaaa tttacggtag atgcggacga ccccggccgc    480
tggcaaccca ccccacctgc ctacatggac ggtattgaac ccactggaa taaaatcagg    540 ccatttgtat tggattcggc agcacagttc aagcccgttc cacctccggc atattccctt    600
gaagaagact ccgcgtttta taagaattaa aagaagtct atgacgtaag gaacaaaatc    660
accgaggaag gcgatagttc cgaagaaatt cagattgccc gcttttggga ttgtaaccct    720
tatgtatcgg ttaccgtgg ccacttgatg ttcgccacca agaaaataac cccaggtgcg    780
cattggatgg gaattgccaa aattgccgca cgtaaaacca acagtgattt tgccaaaacc    840
cttttcgcct ataccaaggc ctcggtagcc atggcggatg cctttatcag ttgttgggac    900
gaaaagtaca gaagcaacct catccgtccg gaaaccgtaa tcaaccaaca tatagacgac    960
agctggaaac cagtgctaca aaccctccg tttccagagt acaccagcgg acatagtgta    1020
gtctcagggg cggcatcggt tgtactgacc gaggtctttg gtgacaattt ctcctttgac    1080
gacgatacgg aagtacctta cggcctacct atccgaagct ttaaatcctt taagcaagct    1140
gccgacgaag cagcgatcag tcgcatgtac ggaggcatac actaccgtgc agctattgaa    1200
gtaggggtaa acaaggcag ggacctaggt accttgtcg taaacaaact acatatgcta    1260
tccgataaga agtagccca aaac    1284

<210> SEQ ID NO 12
<211> LENGTH: 1353
<212> TYPE: DNA
<213> ORGANISM: Zobellia galactanivorans
<220> FEATURE:
<221> NAME/KEY: misc_feature
<223> OTHER INFORMATION: ZgvIPO1 nucleotide sequence with the putative
      native peptide signal sequence (wild-type ZgvIPO1)

<400> SEQUENCE: 12
atgaagaaga ttcttatcgc actaatatcg tttgcttttg cggtttcgtg caaagctcca     60 caaaagaag aacctattaa cattaccccc gaagagcttg acgcttcaat agacagggtg    120
acggaaatta tgatccacga tatctttttcc cctcccgttg cgagtaggat ctttgcctat    180
cccaacgttg ccgcctacga aattgtagcc gccaccaatg acaactacaa ctccttggcc    240
ggccaattga cgggctgac cgccataccg gaacccgata ccactaagac catcaactac    300
gagcttgcag ccgtcgtcgc ccatatggag cttagcaaaa ggttgatttt tctcagaagac    360 cgaatggaat ccctgcgcga tagcctatac atggtttggg aagggaaaaa tcctgttcta    420
ttctccgatt ccaaagccta cggcctacaa gtggccgacc atataggcga atggatgaac    480
aaggacaatt acgcccaaac ccgcaccatg ccgaaattta cggtagatgc ggacgacccc    540
ggccgctggc aacccacccc acctgcctac atggacggta ttgaacccca ctggaataaa    600
atcaggccat ttgtattgga ttcggcagca cagttcaagc ccgttccacc tccggcatat    660
tcccttgaag aagactccgc gttttataaa gaattaaaag aagtctatga cgtaaggaac    720
aaaatcaccg aggaaggcga tagttccgaa gaaattcaga ttgcccgctt tgggattgt    780 aacccttatg tatcggttac ccgtggccac ttgatgttcg ccaccaagaa aataaccccca    840
```

```
ggtgcgcatt ggatgggaat tgccaaaatt gccgcacgta aaaccaacag tgattttgcc      900 aaaaccctttt tcgcctatac caaggcctcg gtagccatgg cggatgcctt tatcagttgt     960
tgggacgaaa agtacagaag caacctcatc cgtccggaaa ccgtaatcaa ccaacatata    1020
gacgacagct ggaaaccagt gctacaaacc cctccgtttc cagagtacac cagcggacat    1080
agtgtagtct caggggcggc atcggttgta ctgaccgagg tctttggtga caatttctcc    1140
tttgacgacg atacggaagt accttacggc ctacctatcc gaagctttaa atcctttaag    1200
caagctgccg acgaagcagc gatcagtcgc atgtacggag gcatacacta ccgtgcagct    1260
attgaagtag gggtaaaaca aggcagggac ctaggtacct tgtcgtaaaa caaactacat    1320
atgctatccg ataagaaagt agcccaaaac taa                                  1353
```

<210> SEQ ID NO 13
<211> LENGTH: 1338
<212> TYPE: DNA
<213> ORGANISM: artificial
<220> FEATURE:
<223> OTHER INFORMATION: ZgvIPO1 nucleotide sequence A with a histidine
      tag sequence

<400> SEQUENCE: 13

```
atgggcagca gccaccatca ccatcaccat ggatccaaag ctccacaaaa agaagaacct       60
attaacatta cccccgaaga gcttgacgct tcaatagaca gggtgacgga aattatgatc     120
cacgatatct tttcccctcc cgttgcgagt aggatctttg cctatcccaa cgttgccgcc     180
tacgaaattg tagccgccac caatgacaac tacaactcct tggccggcca attgaacggg     240
ctgaccgcca taccggaacc cgataccact aagaccatca actacgagct tgcagccgtc     300
gtcgcccata tggagcttag caaaaggttg attttctcag aagaccgaat ggaatccctg     360
cgcgatagcc tatacatggt ttgggaaggg aaaaatcctg ttctattctc cgattccaaa     420
gcctacggcc tacaagtggc cgaccatata ggcgaatgga tgaacaagga caattacgcc     480
caaacccgca ccatgccgaa atttacggta gatgcggacg accccggccg ctggcaaccc     540
accccacctg cctacatgga cggtattgaa ccccactgga taaaaatcag gccatttgta     600
ttggattcgg cagcacagtt caagcccgtt ccacctccgg catattccct tgaagaagac     660
tccgcgtttt ataaagaatt aaaagaagtc tatgacgtaa ggaacaaaat caccgaggaa     720
ggcgatagtt ccgaagaaat tcagattgcc cgcttttggg attgtaaccc ttatgtatcg     780 gttaccccgtg gccacttgat gttcgccacc aagaaaataa ccccaggtgc gcattggatg     840
ggaattgcca aaattgccgc acgtaaaacc aacagtgatt ttgccaaaac ccttttcgcc     900
tataccaagg cctcggtagc catggcggat gcctttatca gttgttggga cgaaaagtac     960
agaagcaacc tcatccgtcc ggaaaccgta atcaaccaac atatagacga cagctggaaa    1020
ccagtgctac aaaccctcc gtttccagag tacaccagcg gacatagtgt agtctcaggg    1080
gcggcatcgg ttgtactgac cgaggtcttt ggtgacaatt tctcctttga cgacgatacg    1140
gaagtacctt acggctacc tatccgaagc tttaaatcct taagcaagc tgccgacgaa    1200 gcagcgatca gtcgcatgta cggaggcata cactaccgtg cagctattga agtagggta    1260
```

```
aaacaaggca gggacctagg tacctttgtc gtaaacaaac tacatatgct atccgataag    1320
aaagtagccc aaaactag                                                  1338

<210> SEQ ID NO 14
<211> LENGTH: 1323
<212> TYPE: DNA
<213> ORGANISM: artificial
<220> FEATURE:
<223> OTHER INFORMATION: ZgvIPO1 nucleotide sequence B with a histidine
      tag sequence

<400> SEQUENCE: 14
atgggcagca gccaccatca ccatcaccat ggatccgaag aacctattaa cattacccccc   60 gaagagcttg acgcttcaat agacagggtg acggaaatta tgatccacga tatctttttcc  120 cctcccgttg cgagtaggat ctttgcctat cccaacgttg ccgcctacga aattgtagcc    180
gccaccaatg acaactacaa ctccttggcc ggccaattga acgggctgac cgccataccg    240
gaacccgata ccactaagac catcaactac gagcttgcag ccgtcgtcgc ccatatggag    300
cttagcaaaa ggttgatttt ctcagaagac cgaatggaat ccctgcgcga tagcctatac    360
atggtttggg aagggaaaaa tcctgttcta ttctccgatt ccaaagccta cggcctacaa    420
gtggccgacc ataggcga atggatgaac aaggacaatt cgcccaaac ccgcaccatg       480 ccgaaattta cggtagatgc ggacgacccc ggccgctggc aacccacccc acctgcctac    540
atggacggta ttgaacccca ctggaataaa atcaggccat ttgtattgga ttcggcagca    600
cagttcaagc ccgttccacc tccggcatat tcccttgaag aagactccgc gttttataaa    660
gaattaaaag aagtctatga cgtaaggaac aaaatcaccg aggaaggcga tagttccgaa    720
gaaattcaga ttgcccgctt tgggattgt aaccctatg tatcggttac ccgtggccac      780
ttgatgttcg ccaccaagaa aataacccca ggtgcgcatt ggatgggaat tgccaaaatt    840
gccgcacgta aaaccaacag tgattttgcc aaaacccttt tcgcctatac caaggcctcg    900
gtagccatgg cggatgcctt tatcagttgt tgggacgaaa agtacagaag caacctcatc    960
cgtccggaaa ccgtaatcaa ccaacatata gacgacagct ggaaaccagt gctacaaacc    1020
cctccgtttc cagagtacac cagcggacat agtgtagtct cagggcggc atcggttgta    1080 ctgaccgagg tctttggtga caatttctcc tttgacgacg atacggaagt accttacggc    1140
ctacctatcc gaagctttaa atcctttaag caagctgccg acgaagcagc gatcagtcgc    1200
atgtacggag gcatacacta ccgtgcagct attgaagtag ggtaaaaca aggcagggac     1260 ctaggtacct tgtcgtaaa caaactacat atgctatccg ataagaaagt agcccaaaac    1320
tag                                                                  1323

<210> SEQ ID NO 15
<211> LENGTH: 38
<212> TYPE: DNA
<213> ORGANISM: artificial
<220> FEATURE:
<223> OTHER INFORMATION: forward primer to clone the ZgvIPO1 nucleotide
      sequence A

<400> SEQUENCE: 15
ggggggggat ccaaagctcc acaaaaagaa gaacctat                            38

<210> SEQ ID NO 16
<211> LENGTH: 40
<212> TYPE: DNA
<213> ORGANISM: artificial
```

```
<220> FEATURE:
<223> OTHER INFORMATION: reverse primer to clone the ZgvIPO1 nucleotide
      sequence A

<400> SEQUENCE: 16 cccccccgaat tcttagtttt gggctacttt cttatcggat                              40
```

BACTERIAL IODOPEROXIDASES FROM ZOBELLIA GALACTANIVORANS, METHODS OF PREPARATION AND USES THEREOF

RELATED APPLICATION DATA

This application is a National Stage Application under 35 U.S.C. 371 of co-pending PCT application PCT/EP2012/063144 designating the United States and filed Jul. 5, 2012; which claims the benefit of EP application number 11305864.8 and filed Jul. 5, 2011 each of which are hereby incorporated by reference in their entireties.

The present invention relates to the technical field of halide oxidation during chemical or biochemical processes, using haloperoxidases.

More specifically, the present invention relates to iodide oxidation, using specific and efficient iodoperoxidases from the bacteria *Zobellia galactanivorans*, isolated nucleic acids encoding same, as well as methods for preparing these enzymes.

Moreover, the present invention is directed to the use of such iodoperoxidases in a wide range of industrial, pharmaceutical, medical, cosmetics, and ecological applications, as well as in the food industry.

Halogenated compounds are abundantly found in nature, and play various biological functions when produced by an organism, ranging from chemical defense to signaling molecules. Most organisms capable of incorporating halogens into organic compounds are of marine origin, such as algae and bacteria, and have evolved such capacity thanks to specific enzymes, namely, haloperoxidases.

Haloperoxidases (or HPOs) catalyze, in the presence of hydrogen peroxide, the oxidation of halides according to the following reaction:

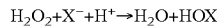

wherein $X^-$ represents a halide ion and is $Cl^-$ or $Br^-$ or $I^-$. A variety of halocarbons can subsequently be generated if the appropriate nucleophilic acceptors are present.

Said haloperoxidases are named according to the most electronegative halide that they can oxidize: chloroperoxidases (CPOs) can catalyze the oxidation of chloride as well as of bromide and iodide, bromoperoxidases (BPOs) react with bromide and iodide, whereas iodoperoxidases (IPOs) are the most specific as they only react with iodide.

Of particular interest is a specific subclass of HPOs that binds a vanadate ion, better known as vanadium-dependant HPOs (or vHPOs): the ability of these enzymes to halogenate a broad range of organic compounds of both commercial and pharmaceutical interest, as well as their high stability towards high temperatures, oxidative conditions and in the presence of organic solvents, make them good candidates for use in industrial biotransformations (Vilter, 1995; Butler et al., 2001).

These properties have elicited detailed structural and mechanistic studies on several vHPOs, namely the CPO from the fungus *Curvularia inaequalis* (Messerschmidt and Wever, 1996), the BPOs from the red algae *Corallina pilulifera* (Shimonishi et al., 1998; Ohshiro et al., 2002) and *Corallina officinalis* (Isupov et al., 2000; Carter et al., 2002) or from the fucalean brown algae *Fucus distichus* (Vreeland et al., 1998) and *Ascophyllum nodosum* (Weyand et al., 1999), as well as the IPOs from *Laminaria digitata* (Colin et al., 2005).

International Patent Application PCT/IB2003/006405, published under No WO2004/078976, describes new bromo- and iodoperoxidases isolated from the brown algae *Laminaria digitata*. However, WO2004/078976 provides only isolation and subsequent purification of IPOs from the algal sporophytes in order to characterize their biochemical properties and specific activities. Recombinant expression of the IPOs from *L. digitata* has not been demonstrated.

The present invention provides for the first time a iodoperoxidase from *Zobellia galactanivorans*. This is also the first report demonstrating a successful recombinant expression of a iodoperoxidase.

More precisely, the present invention provides vanadium-dependant iodoperoxidases (vIPOs) of *Zobellia galactanivorans* (ZgvIPOs), said enzymes having highly specific and highly efficient activities for oxidizing iodide.

In the context of the invention, the terms "activity", "function", "biological activity", and "biological function" are equivalent and have to be understood as it is well known in the art. Preferably, such an activity is enzymatic. That is in the context of the invention, the activity exhibited by the proteins of the invention is one of a iodoperoxidase, such as described above, and can be detected according to the protocol described in paragraph I.4 of the examples below, and/or measured according to the protocol based on the iodination of thymol blue described by Verhaeghe et al. (2008).

A first aspect of the invention is related to an isolated iodoperoxidase of *Zobellia galactanivorans*.

By "isolated", it is meant free from its natural environment. More precisely, by "isolated", it is meant at least partially purified away from other components. Preferably, "isolated" means that at least one order of magnitude of purification is achieved, preferably two or three orders of magnitude, and most preferably four or five orders of magnitude of purification of the starting material or of the natural material. Thus, the term "isolated" as utilized herein does not necessarily mean that the material of interest is 100% purified and that said material thus excludes any other material.

Preferably, "an isolated iodoperoxidase of *Z. galactanivorans*" (ZgIPO) refers to a proteinaceous composition comprising an IPO extracted from *Z. galactanivorans* cells or from recombinant host cells expressing an IPO of *Z. galactanivorans*, wherein said iodoperoxidase is purified to any degree relative to its naturally-obtainable state, i.e., is free from its natural environment. This does not mean in all cases that the isolated ZgIPO is free from any other compounds or impurities, provided the enzyme activity is the only one to be retained by the composition, as may be assessed, for example, by the protein assays described in paragraph I.4 of the examples below, or as would be known to one of ordinary skill in the art for the desired IPO. Substantially pure compositions of at least about 90 to 95% homogeneity are preferred, and 98 to 99% or more homogeneity are yet preferred.

Methods for obtaining said iodoperoxidase are described below.

Once purified, partially or to homogeneity, the IPO protein from *Z. galactanivorans* may then be used as described below.

The terms "protein", "peptide" and "polypeptide" refer to a sequence of amino acids or residues having no specific length. Thus, peptides, oligopeptides, polypeptides and proteins are encompassed by this definition. Also covered by this definition, are polypeptides having undergone post-translational modifications such as polypeptides having covalent attachment of glycosyl groups, acetyl groups, phosphate groups, lipid groups, and the like.

In other words, in the context of the invention, the terms "protein", "peptide" and "polypeptide" are used interchangeably to refer to an "amino acid sequence". Such sequence is preferably that of an enzyme and, more preferably, that of an IPO, such as defined above.

Preferably, the isolated IPO of *Z. galactanivorans* according to the present invention is selected from a iodoperoxidase comprising at least one sequence selected from the sequences SEQ ID No 1, SEQ ID No 2, SEQ ID No 3, SEQ ID No 4, SEQ ID No 5, and functional fragments and functional variants thereof.

An IPO according to the invention can contain a signal peptide sequence useful for expression of said enzyme in a host cell, such as the putative native signal peptide sequence of ZgvIPO1 of sequence MKKILIALISFAFAVSCKAPQK (SEQ ID No 6; such as IPO of sequence SEQ ID No 3), or a protein purification tag, such as a histidine tag (e.g. of sequence SEQ ID No 8: MGSSHHHHHHGS; such as IPO of sequence SEQ ID No 4 or SEQ ID No 5), in the N-Terminal extremity and/or C-Terminal extremity of said IPO.

Yet preferably, the isolated IPO of *Z. galactanivorans* according to the present invention is selected from a iodoperoxidase having a sequence selected from:
  SEQ ID No 1, wherein a methionin amino-acid can be further present as a translation start signal in the N-terminal extremity of said SEQ ID No 1,
  SEQ ID No 2, wherein a methionin amino-acid can be further present as a translation start signal in the N-terminal extremity of said SEQ ID No 2,
  SEQ ID No 3,
  SEQ ID No 4,
  SEQ ID No 5,
and functional fragments and functional variants thereof.

By "functional fragments" of an amino acid sequence of reference having a biological activity of interest (as defined above), it is meant parts of this amino acid sequence of reference, said parts comprising at least all the regions essential for exhibiting the biological activity of the amino acid sequence of reference. These parts of sequences can be of various lengths, provided the biological activity of the amino acid sequence of reference is retained by said parts.

The definition above can be applied mutatis mutandis to "functional fragments" of a nucleic acid of reference, said nucleic acid of reference encoding a protein having a biological function of interest.

By "functional variants" of an amino acid sequence of reference having a biological activity of interest (as defined above), it is meant proteins that structurally differ from the amino acid sequence of reference but that generally retain all the essential functional characteristics of said amino acid sequence of reference. A variant of a protein may be a naturally-occurring variant or a non-naturally occurring variant. Such non-naturally occurring variants of the reference protein can be made, for example, by mutagenesis techniques on the encoding nucleic acids, such as random mutagenesis or site-directed mutagenesis. More preferably, said non-naturally occurring variants are generated by site-directed mutagenesis.

Structural differences may be limited in such a way that the amino acid sequence of reference and the amino acid sequence of the variant may be closely similar overall, and identical in many regions.

Structural differences may result from conservative or non-conservative amino acid substitutions, deletions and/or additions between the amino acid sequence of reference and the variant. The only proviso is that, even if some amino acids are substituted, deleted and/or added, the biological activity of the amino acid sequence of reference is retained by the variant, that is to say in the context of the present invention, the variant retains a iodoperoxidase activity, as defined above. The activity of said variant may however differ in its efficiency of iodination compared to the activity of the amino acid sequence of reference.

An isolated IPO according to the present invention is preferably encoded by a nucleic acid comprising at least one sequence selected from the sequences SEQ ID No 10, SEQ ID No 11, SEQ ID No 12, SEQ ID No 13, SEQ ID No 14, functional fragments and functional variants thereof, and complementary sequences thereof.

A nucleic acid according to the invention can contain a nucleotide sequence encoding a signal peptide sequence useful for expression of said enzyme in a host cell, such as the putative native signal peptide sequence of ZgvIPO1 of sequence ATGAAGAAGATTCTTATCGCAC-TAATATCGTTTGCTTTTGCGGTTTCGTG-CAAAGCTCCACAAAAA (SEQ ID No 7; such as the IPO sequence SEQ ID No 12), or a nucleotide sequence encoding a protein purification tag, such as a histidine tag (SEQ ID No 9; such as the IPO sequence SEQ ID No 13 or SEQ ID No 14), in the 5' and/or 3' termini of the selected sequence.

Preferably, the isolated IPO of *Z. galactanivorans* according to the present invention is encoded by a nucleic acid consisting of a sequence selected from:
  SEQ ID No 10, wherein a start codon can be further present in the 5' extremity and a stop codon can be further present in the 3' extremity of said SEQ ID No 10,
  SEQ ID No 11, wherein a start codon can be further present in the 5' extremity and a stop codon can be further present in the 3' extremity of said SEQ ID No 11,
  SEQ ID No 12,
  SEQ ID No 13,
  SEQ ID No 14,
functional fragments and functional variants thereof, and complementary sequences thereof.

Start codons include, but are not limited to, the codons (or trinucleotides, or triplets) ATG, AUG, TTG, UUG, GTG, GUG, CTG and CUG, and can be selected by the person skilled in the art based on the host cell wherein said nucleic acid will be translated. Stop codons include, but are not limited to, the codons TAG, UAG, TAA, UAA, TGA and UGA and can be selected by the person skilled in the art based on the host cell wherein said nucleic acid will be translated.

As used herein, the terms <<nucleic acid>> or <<nucleotide sequence>> are used interchangeably, and refer to a precise succession of natural nucleotides (namely, A, T, G, C and U) or non-natural nucleotides, corresponding to a single-stranded or double-stranded DNA such as a cDNA, a genomic DNA, or a plasmidic DNA, and the transcription product of said DNA, such as an RNA. According to the invention, the term "oligonucleotide" preferably refers to a nucleic acid of less than 50 nucleotides in length, while the term "polynucleotide" preferably refers to a nucleic acid of greater than 50 nucleotides in length.

The nucleotide sequences of the present invention may be prepared by any known method including, but not limited to, any synthetic method, any recombinant method, any ex vivo generation method and the like, as well as combinations thereof.

As used herein, the term "complementary" means that, for example, each nucleotide of a first nucleic acid sequence is paired with the complementary base of a second nucleic acid sequence whose orientation is reversed. Complementary nucleotides are A and T (or A and U) or C and G.

"Variants" of nucleic acid according to the present invention include, but are not limited to, nucleic acid sequences which are at least 95% identical after alignment to the reference nucleic acid encoding the reference protein. These variants can also have 96%, 97%, 98%, 99%, and 99,999% sequence identity to the nucleic acid encoding the reference protein.

Nucleotide changes present in a nucleic acid variant may be silent, which means that these changes do not alter the amino acid sequence encoded by the reference nucleic acid.

Also encompassed by the term "variants" of a nucleic acid of reference, are nucleic acids which can hybridize to said nucleic acid of reference. Hybridizing nucleic acids can be useful as probes or primers, for example.

For instance, such hybridizing nucleic acids may be at least 10 nucleotides in length or preferably, at least 17 nucleotides in length. They may also be at least 25 or at least 50 nucleotides in length.

In the context of the present invention, hybridizing nucleic acids will preferably hybridize to the nucleic acid of reference under stringent hybridization conditions. One example of stringent hybridization conditions is where attempted hybridization is carried out at a temperature of from about 35° C. to about 65° C. using a salt solution which is about 0.9 molar. However, the skilled person will be able to vary such conditions appropriate in order to take into account variables such as probe length, base composition, type of ions present, etc.

Examples of hydridizing nucleic acids include, but are not limited to, the nucleic acids of sequence SEQ ID No 15 and SEQ ID No 16.

Identity between nucleic acid or amino acid sequences can be determined by comparing a position in each of the sequences which may be aligned for the purposes of comparison. When a position in the compared sequences is occupied by the same nucleotide or amino acid, then the sequences are identical at that position. A degree of sequence identity between nucleic acids is a function of the number of identical nucleotides at positions shared by these sequences. A degree of identity between amino acid sequences is a function of the number of identical amino acid sequences that are shared between these sequences.

To determine the percentage of identity between two amino acid sequences or two nucleic acid sequences, the sequences are aligned for optimal comparison. For example, gaps can be introduced in the sequence of a first amino acid sequence or a first nucleic acid sequence for optimal alignment with the second amino acid sequence or second nucleic acid sequence. The amino acid residues or nucleotides at corresponding amino acid positions or nucleotide positions are then compared. When a position in the first sequence is occupied by the same amino acid residue or nucleotide as the corresponding position in the second sequence, the molecules are identical at that position.

The percentage of identity between the two sequences is a function of the number of identical positions shared by the sequences. Hence % identity=number of identical positions/ total number of overlapping positions×100.

In this comparison, the sequences can be of the same length or may be of different lengths.

Optimal alignment of sequences may be conducted by the global homology alignment algorithm of Needleman and Wunsch (1972), by computerized implementations of this algorithm or by visual inspection. The best alignment (i.e., resulting in the highest percentage of identity between the compared sequences) generated by the various methods is selected.

In other words, the percentage of sequence identity is calculated by comparing two optimally aligned sequences, determining the number of positions at which the identical nucleotide occurs in both sequences to yield the number of matched positions, dividing the number of matched positions by the total number of positions and multiplying the result by 100 to yield the percentage of sequence identity. The same process can be applied to protein sequences.

In the context of the present invention, the nucleic acid variants are "functional", that is to say they encode amino-acid sequences having a biological activity of interest as defined above.

The nucleic acids disclosed herein are advantageously comprised in a recombinant vector.

The terms "vector", and "plasmid" herein relate to the same tool which is useful for performing procedures of molecular biology and genetic recombination. Such tool is commonly used and very well known in the art. A nucleic acid of interest can thus be inserted into a vector capable of replication in order to amplify said nucleic acid, or to express the protein encoded by said nucleic acid. These vectors are better known as "cloning vectors" (to amplify a nucleic acid) or "expression vectors" (to express a protein), and are publicly available. Such vectors include, without limitation, plasmid vectors, cosmids, YACS, viral vectors (adenovirus, retrovirus, EBV episome), and phage vectors. In particular, the above-mentioned vectors are said to be recombinant in that they are not found in nature combined to said nucleic acid of interest.

Methods for inserting a nucleic acid into such vectors are known to those skilled in the art. Generally, a nucleic acid is inserted into one or more restriction endonuclease site(s) using appropriate techniques known in the art, e.g. via ligation (see, for example, the techniques described in Sambrook et al., 2001; Ausubel et al., 2011). Nucleotide sequences allowing the transcription of said nucleic acid, the expression and/or purification of the protein encoded by said nucleic acid are preferably also contained in the recombinant vector of the invention. These sequences include, generally and without limitation, at least one sequence selected from one or more signal peptide sequence(s), an origin of replication, one or more gene(s) marker(s) selection, an enhancer element, a promoter, a transcription terminator, and possibly a sequence allowing purification of a protein. The insertion of such sequences in said vector can be done via standard ligation techniques known to those skilled in the art, such as mentioned above. It is additionally known to those skilled in the art that, depending on the nucleotide sequences present in the vector, said vector can replicate in different host cells, and/or the protein encoded by said nucleic acid can be expressed in different host cells.

The recombinant vector is advantageously comprised in a recombinant host cell, such as a prokaryotic or a eukaryotic cell.

As used herein, the terms "host cell", "cell" and "cell line", can be used interchangeably, and refer to a prokaryotic or a eukaryotic cell in which the recombinant vector of the invention can be introduced, such as to amplify the nucleic acid as described above, and/or to express the protein encoded by said nucleic acid. To this end, a host cell may be "transfected" or "transformed" by a process known to those skilled in the art by which said vector is transferred or introduced into the host cell. Examples of such methods include, without limitation, electroporation, lipofection, calcium phosphate transfection, transfection using DEAE dextran, microinjection, and biolistics.

The choice of the host cell can be correlated to the choice of said vector, depending on the selected use, namely the cloning of the nucleic acid or the expression of the protein encoded by said nucleic acid. The skilled person will be able to choose the appropriate host cell among the many cell lines that are publicly available, notably via the American Type Culture Collection (ATCC) (www.ATCC.org).

Examples of prokaryotic cells include, without limitation, bacteria such as Gram-negative bacteria of the genus *Escherichia* (eg *E. coli* RR1, LE392, B, X1776, W3110, DH5 alpha, JM109, KC8), *Serratia Pseudomonas, Erwinia Methylobacterium, Rhodobacter, Salmonella* and *Zymomonas*, and Gram positive bacteria of the genus *Corynebacterium, Brevibacterium, Bacillus, Arthrobacter*, and *Streptomyces*.

Examples of eukaryotic cells include, without limitation, cells isolated from fungi, plants, and animals. Such cells notably include, yeasts of the genus *Saccharomyces*, cells of the fungi *Aspergillus, Neurospora, Fusarium* and *Trichoderma*, animal cells such as HEK293 cells, NIH3T3, Jurkat, MEF, Vero, HeLa, CHO, W138, BHK, COS-7, MDCK, C127, Saos, PC12, HKG, and insect cells Sf9, Sf21, Hi Five™ or of *Bombyx mori*. The use of insect cells is particularly described in the manual "*Baculovirus Expression Vectors: A Laboratory Manual*", David R. O'Reilly et al. Oxford University Press, USA (1993).

In a second aspect of the invention, the present invention concerns an isolated nucleic acid encoding a iodoperoxidase of *Z. galactanivorans*, such as defined above.

Preferably, said nucleic acid comprises at least one sequence selected from the sequences SEQ ID No 10, SEQ ID No 11, SEQ ID No 12, SEQ ID No 13, SEQ ID No 14, functional fragments and functional variants thereof, and complementary sequences thereof.

A nucleic acid according to the invention can contain a nucleotide sequence encoding a signal peptide sequence useful for expression of said enzyme in a host cell, such as the putative native signal peptide sequence of ZgvIPO1 of sequence ATGAAGAAGATTCTTATCGCAC-TAATATCGTTTGCTTTTGCGGTTTCGTG-CAAAGCTCCACAAAAA (SEQ ID No 7; such as the IPO sequence SEQ ID No 12), or a nucleotide sequence encoding a protein purification tag, such as a histidine tag (SEQ ID No 9; such as the IPO sequence SEQ ID No 13 or SEQ ID No 14), in the 5' and/or 3' termini said selected sequence.

Preferably, said nucleic acid consists of a sequence selected from the sequences:
SEQ ID No 10, wherein a start codon can be further present in the 5' extremity and a stop codon can be further present in the 3' extremity of said SEQ ID No 10,
SEQ ID No 11, wherein a start codon can be further present in the 5' extremity and a stop codon can be further present in the 3' extremity of said SEQ ID No 11,
SEQ ID No 12,
SEQ ID No 13,
SEQ ID No 14,
functional fragments and functional variants thereof, and complementary sequences thereof.

Definitions of nucleic acids, start and stop codons, have been provided above.

The term "isolated" as used herein means that a nucleic acid has been removed from its original environment in which it is naturally present. Indeed, a nucleic acid, when present in a plant, bacteria or animal in its naturally state, is not considered to be isolated, whereas the same nucleic acid, when separated from the adjacent nucleic acid sequences in which it is naturally inserted in the genome of said plant, bacteria or animal, is considered as being "isolated".

The term "isolated" is not meant to exclude artificial or synthetic mixtures with other compounds, or the presence of impurities which do not interfere with the biological activity and which may be present, for example, due to incomplete purification, addition of stabilizers or mixtures with pharmaceutically acceptable excipients and the like.

Functional variants of said nucleic acids have also been described herein above.

A recombinant vector comprising an isolated nucleic acid encoding a iodoperoxidase of *Z. galactanivorans*, and a recombinant host cell comprising said recombinant vector, both as defined above, are also encompassed as further aspects of the present invention.

According to yet a further aspect, the invention is related to a method for obtaining an isolated iodoperoxidase of *Z. galactanivorans*, such as defined above.

Such method comprises at least the steps of:
a) cloning an isolated nucleic acid as defined above, into a recombinant expression vector;
b) transforming a recombinant host cell with said recombinant expression vector; and
c) expressing said isolated nucleic acid from said recombinant host cell, so as to obtain said iodoperoxidase.

The recombinant vector used in steps a) and b) and the recombinant host cell used in steps b) and c) are as defined above.

In particular, the iodoperoxidase of step c) can be obtained by recovering said enzyme from the host cells if the IPO is expressed intracellularly, and/or from the culture medium in which the host cells are cultured if the IPO is expressed extracellularly.

The iodoperoxidase obtained in step c) can be advantageously purified, in a further step of said method, defined as step d). Preferably, said purification step allows the obtention of a 100%-purified or almost 100%-purified protein.

According to an embodiment of the method of the invention, the host cell as described above is cultured in a suitable culture medium under conditions permitting the expression of the nucleic acid, and thus of the iodoperoxidase. The skilled person in the art may use any conventional method allowing the isolation and/or purification of said enzyme. For example, if the protein was expressed in a dissolved form in host cells, the latter are recovered by centrifugation and suspended in a buffer, then a cell-free extract is obtained by destroying cells through example of an ultrasonic homogenizer. From the supernatant obtained by centrifugation of this extract, a purified sample can be obtained using a conventional method or combination of conventional methods to isolate and purify the protein of the invention. These methods include, without limitation, solvent extraction, salting out with ammonium sulphate, desalting, precipitation with organic solvent, gel filtration, preparative electrophoresis, isoelectric focusing, ultrafiltration, various chromatographic methods such as ion exchange chromatography (anionic, using for example a resin such as diethylaminoethyl (DEAE) Sepharose; or cationic, by using for example a resin such as S-Sepharose (Pharmacia)), hydrophobic chromatography (using for example a resin such as butyl sepharose or phenyl sepharose), affinity chromatography using antibodies, adsorption chromatography, chromatofocusing, high performance liquid chromatography (HPLC) and reversed phase HPLC.

Moreover, if a nucleotide sequence allowing purification of the protein, such as a histidine tag, is present in the recombinant vector or in the nucleic acid of the invention, as described above, the protein produced can be recovered by cleavage of said sequence through a specific protease (thrombin, trypsin, protease TEV, etc).

According to one embodiment, a iodine salt of formula $I^-M^+$ is used during step d), $M^+$ being an alkaline metal selected from $K^+$, $Na^+$, and $Li^+$.

In the case where a chromatographic method is used in step d), one or more substeps can be performed and include, without limitation, the binding of the obtained iodoperoxidase on a solid support, such as a chromatography column, a washing step, and an elution step. Said substeps can be repeated in order to achieve a 100% or almost 100% purification of the isolated protein.

Advantageously, the iodine salt as defined above is used during the elution substep of step c).

An example of a method allowing the obtention of an isolated iodoperoxidase of *Z. galactanivorans* is described in paragraph I.4 of the examples below.

In another aspect, the present invention is directed to uses of an isolated iodoperoxidase of *Z. galactanivorans*.

This enzyme can be used in a number of industrial, pharmaceutical, medical, cosmetics and ecological applications, as well as in the food industry.

Indeed, the IPO of the invention can suitably be used for any purpose to which prior art haloperoxidases have been used, and more specifically wherein iodide is used.

In one embodiment, the IPO according to the present invention is useful for obtaining iodinated organic compounds of interest by iodinating non-iodinated organic compounds.

As used herein, the terms "organic compounds" refer to gaseous, liquid, or solid chemical compounds whose molecules contain carbon.

An example of iodination of non-iodinated organic compounds (RH) is as follows, using the iodoperoxidase of the invention:

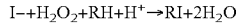

$$I^- + H_2O_2 + RH + H^+ \rightarrow RI + 2H_2O$$

wherein RI represents a iodinated organic compound.

More particularly, said iodinated organic compounds of interest include, without limitation, active organic compounds and chemical intermediates used during organic chemical synthesis. Said active organic compounds include, without limitation, desinfectants, nutrients, pesticides, drugs, antibiotics, advantageously plant antibiotics, antioxydants, adhesives, and radiocontrast agents.

Examples of iodinated compounds of interest have been reviewed by La Barre et al. (2010), and include, but are not limited to, phenolic compounds (e.g. mono-, di-, tri-, tetra-iodophloroglucinol, dibromoiodophénol and polymers thereof, as well as iodinated phlorotannins such as iodinated fuhalols, phlorethols, fucols, fucophlorethols, eckols and carmalols), volatile hydrocarbon compounds (e.g. iodoform, iodomethane, diiodomethane, bromoiodomethane, iodoethane, iodopropane, iodobutane, etc), terpenes, amino-acids derivatives (e.g. mono- and diiodotyrosine, which are thyroxine precursors) and fatty acids derivatives (e.g. eiseniaiodides).

More specifically, iodomethane, diiodomethane, iodoform can be used as desinfectants or pesticides. Iodomethane, also known as methyl iodide, can additionally be used as a chemical intermediate during organic chemical synthesis, notably for methylating other compounds such as phenols, carboxylic acids, ammonia and derived amines, and for the industrial-scale production of acetic acid and acetic anhydride.

Examples of radiocontrast agents according to the invention include, but are not limited to, 1,3,5-triiodobenzène and derivatives thereof, such as the ionic agents diatrizoate, metrizoate and ioxaglate, and the non-ionic agents ioversol, iopamidol, iohexyl, ioxilan, iopromide and iodixanol.

Such agents can be used for X-Ray imagery, such as fluoroscopy.

Additionally, the IPO of the invention can be used to produce adhesives, useful for example in band-aids, due to the capacity of the enzyme to catalyze oxidative cross-linking of natural organic compounds.

In another embodiment, the above-defined IPO can be used for trapping iodine, preferably during bioremediation such as water treatment.

By "bioremediation", it is meant herein the removal of pollutants via a biological molecule, i.e., an enzyme. Radioactive iodine can be cited as an example of pollutant in the above context.

In yet another embodiment, the IPO of *Z. galactanivorans* can be used for the in situ production of antibiotic compounds, for example in antifouling treatment of boats.

The present invention is illustrated, while not being limited, by the following figures:

FIG. 1. Polyacrylamide gel electrophoresis analysis of the NI-sepharose eluted protein fractions during recombinant ZgvIPO1 purification.

The polyacrylamide gel was stained with Coomassie brilliant blue R-250 to reveal the presence of the eluted proteins. ZgvIPO1 indicates the presence of the overexpressed iodoperoxidase enzyme.

Lanes 1 to 30: eluted protein fractions, I: Injected diluted crude extract, M: Precision Plus Protein™ Standards (Bio-Rad Laboratories)

Figure 2A:
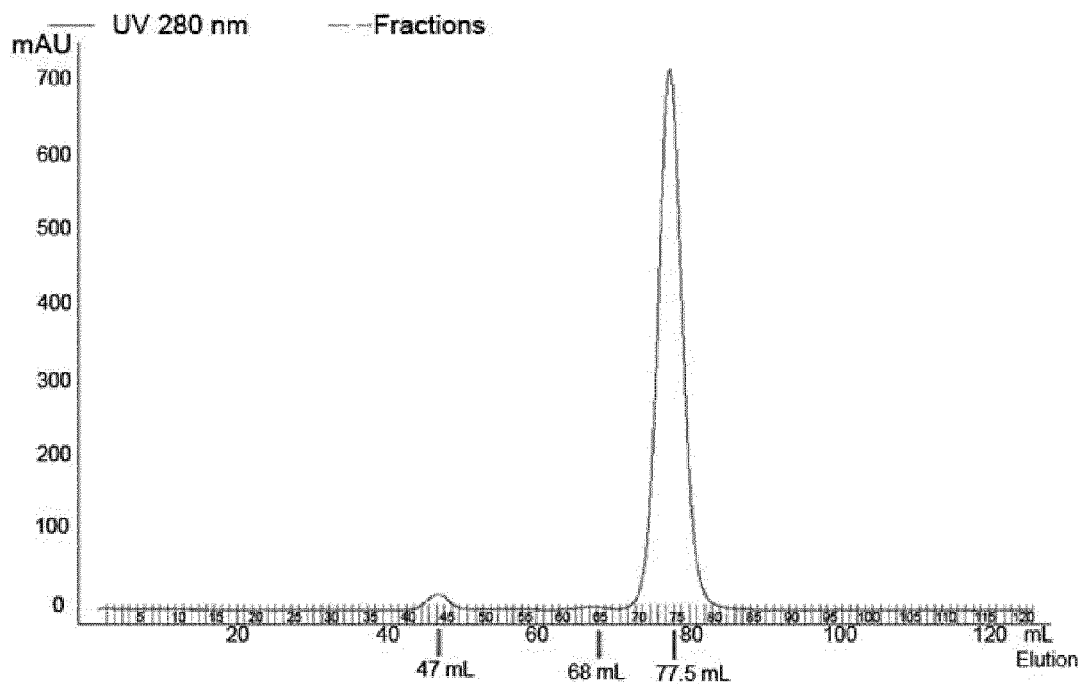
Figure 2B:
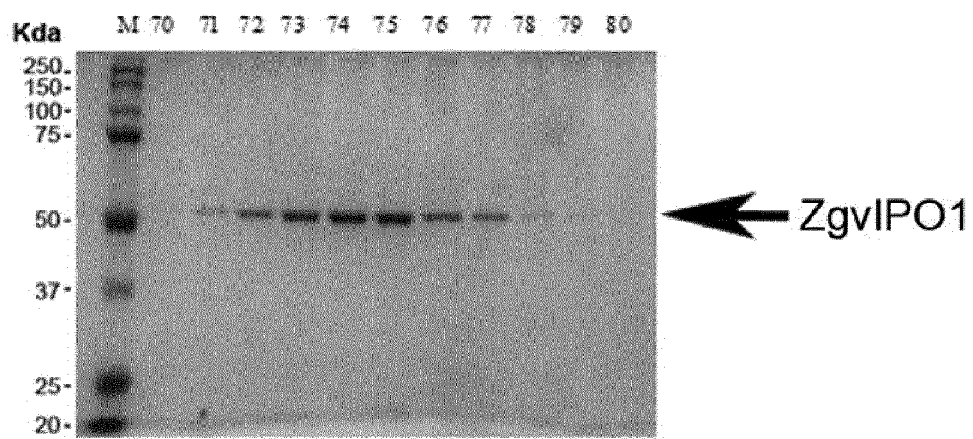

FIG. 2. Size chromatography purification of recombinant ZgvIPO1 protein. FIG. 2A: Superdex 200 purification chromatogram; FIG. 2B: Coomassie blue staining, M: Precision Plus Protein™ Standards (Bio-Rad Laboratories).

Figure 3:
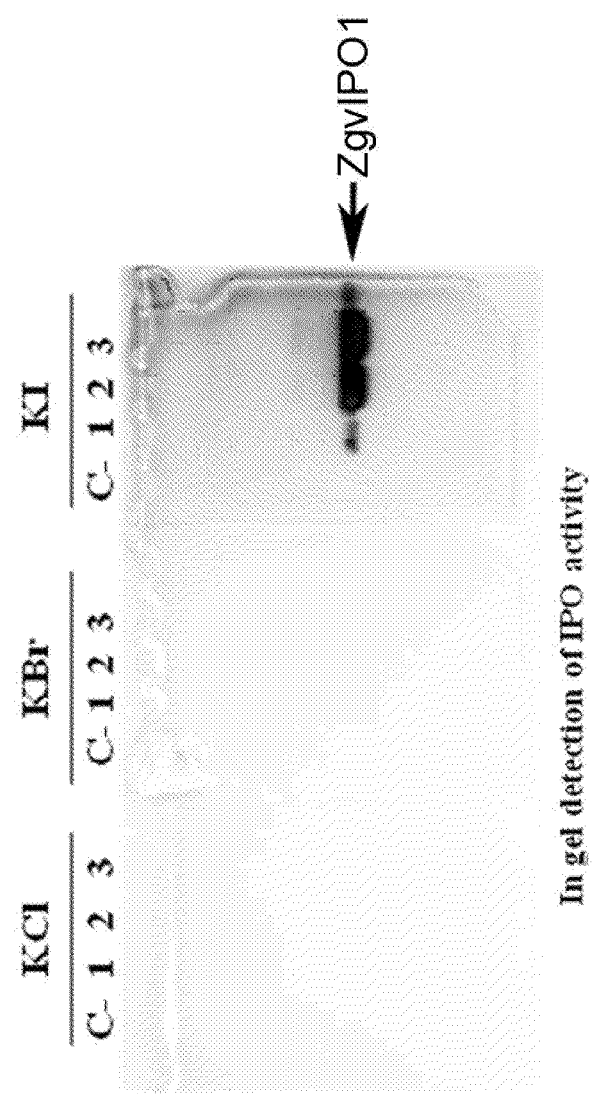

FIG. 3. In-gel haloperoxidase assay of the purified recombinant ZgvIPO1 under non-denaturing PAGE electrophoresis.

Polyacrylamide gels were loaded with MilliQ water (lane C–) as a negative control, and with 1 µL of the purified recombinant ZgvIPO1 enzyme (lane 1), 5 µL of the purified ZgvIO1 enzyme (lane 2), and 10 µL of the purified ZgvIPO1 enzyme (lane 3), and subsequently stained for chloroperoxidase activity (KCl lanes), bromoperoxidase activity (KBr lanes), and for iodoperoxidase activity (KI lanes).

Figure 4:
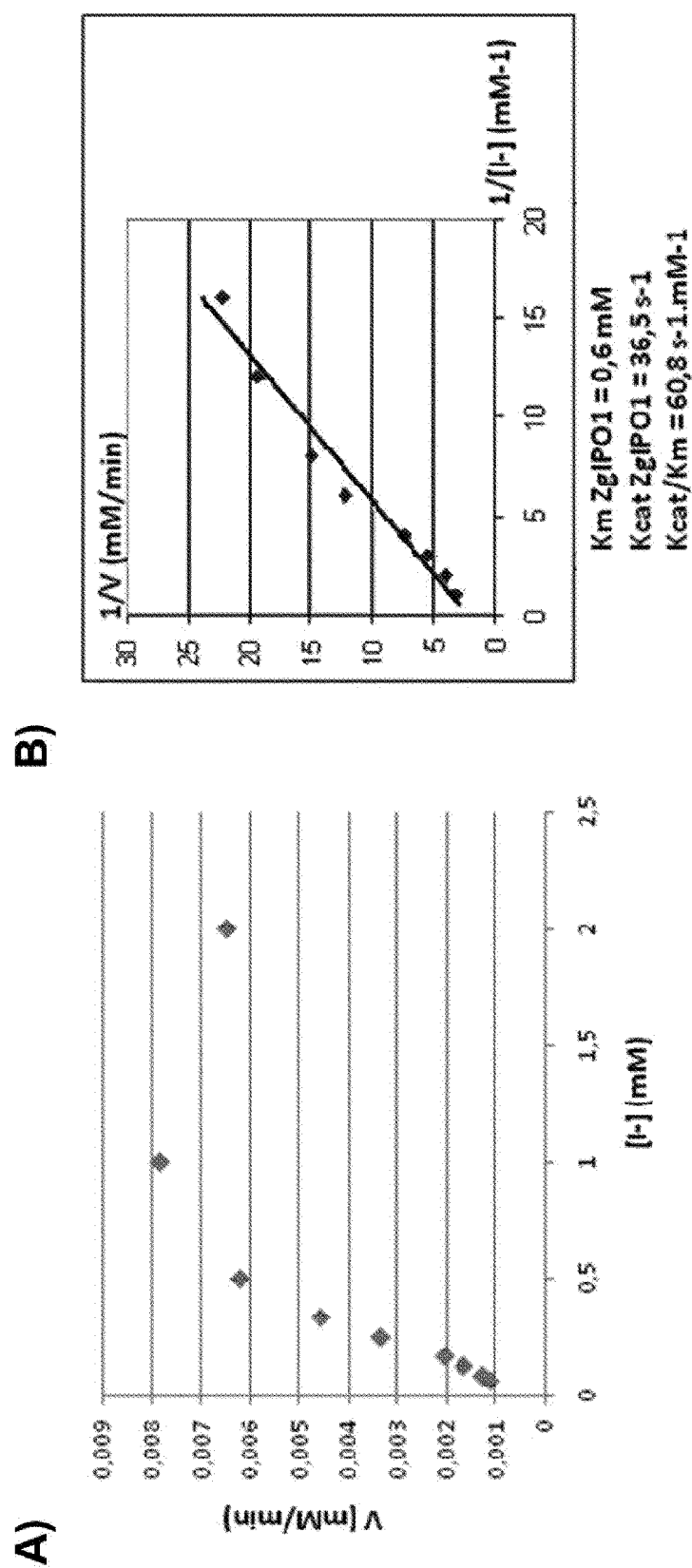

FIG. 4. Steady-state analysis (A) and kinetics parameters determination (B) of the activity of the recombinant purified ZgvIPO1 at various iodide concentrations, using the thymol Blue colorimetric assay.

Figure 5:
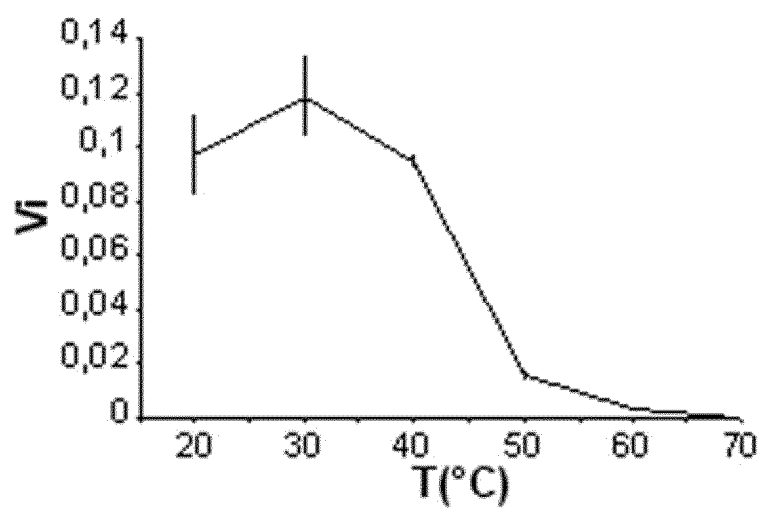

FIG. 5. Iodoperoxidase initial velocity of the purified ZgvIPO1 as a function of temperature at pH 7.2. Error bars indicate standard deviations (n=3).

Figure 6:
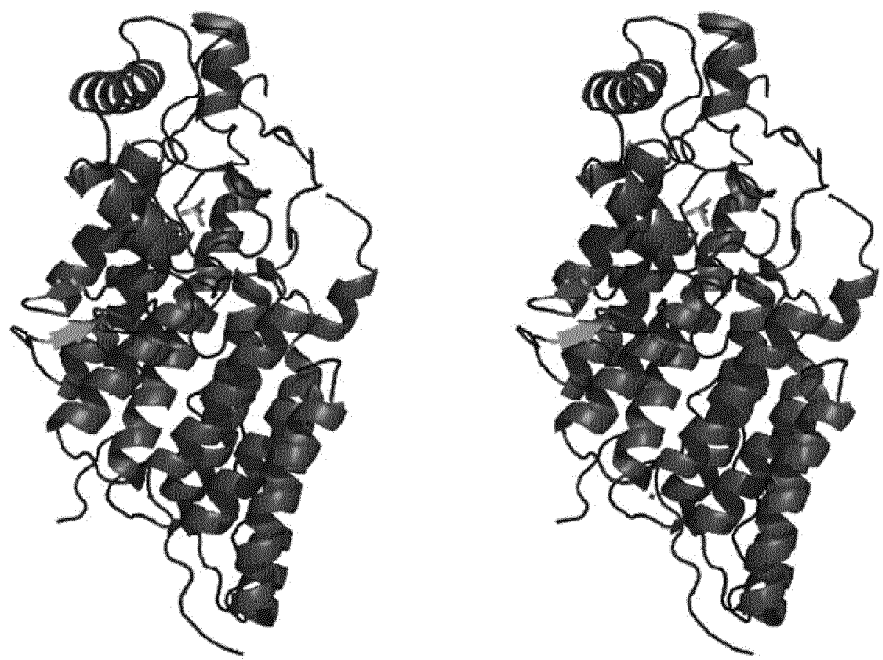

FIG. 6. Structure model of the ZgvIPO1 protein presented as a stereo view. Secondary structure assignment: α-helices are shown in dark grey, and β-strands and coils in light grey.

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

EXAMPLES

I. Experimental Procedures

I.1. Isolation of Bacterial Material and Genomic DNA

The type strain Dsij$^T$ of *Zobellia galactanivorans* was isolated from a red alga (Barbeyron et al. 2001) and grown in ZoBell medium 2216E (ZoBell, 1941) at 20° C. The genomic DNA was isolated as described by Barbeyron et al. (2001) and fully sequenced (Barbeyron et al., unpublished data).

I.2. ZgvIPO1 Cloning and Sequencing

The ZgvIPO1 gene was identified on the genome of *Z. galactinovorans* by sequence similarities with available vHPO proteins using BLASTX program (Altschul et al., 1997). The *Z. galactinovorans* genomic DNA was therefore used as a template for polymerase chain reaction (PCR) amplification of the ZgvIPO1 gene fragment, using the primers of sequence SEQ ID No 15 (forward primer of sequence 5' GGGGGGGGATCCAAAGCTCCACAAAAA-GAAGAACCTAT 3', comprising the BamHI restriction site), and SEQ ID No 16 (reverse primer of sequence 5' CCCCCCGAATTCCTAGTTTTGGGC-TACTTTCTTATCGGAT 3', comprising the EcoRI restriction site).

The PCR was performed using Pfu DNA polymerase, according to the Manufacturer's protocol (Promega) and the PCR product was cloned using a medium throughput cloning program described in Groisillier et al. (2010).

Briefly, the PCR reaction contained 1 μL of *Z. galactinovorans* genomic DNA, 5 μL of each primer (10 μM each), 1 μL dNTPs (0.10 mM), 5 μL reaction 10× buffer with MgSO$_4$, 3 μL Pfu DNA polymerase, and 35 μL of PCR grade water. The cycling conditions were 96° C. for 2 minutes, followed by 35 cycles of 96° C. for 15 s, 60° C. for 30 s, and 72° C. for 6 minutes, terminating at 72° C. for 4 minutes.

A 1311 bp PCR amplicon was then digested by the BamHI and EcoRI restrictions enzymes and cloned into the vector pFO4, a modified expression vector of pET15b (Novagen, USA), in order to be compatible with the BamHI/EcoRI ligation strategy (Groisillier et al. 2010). This expression vector generates a hexa-histidine tail at the N-terminal of recombinant protein, without modifying the recombinant protein activity. This cloning resulted in a gene encoding the ZgvIPO1 protein, without the first 17 amino-acids coding for the putative signal peptide, flanked by an N-terminal hexa-histidine tag. The pFO4-ZgvIPO1 vector was first introduced into *Escherichia coli* DH5α, for standard plasmid amplification and sequencing of both strands of the gene was carried out using the ABI Prism 3100 genetic analyzer (Applied Biosystems, CA, USA).

I.3. Recombinant Overexpression of ZgvIPO1 in *E. coli* and Purification

The pFO4-ZgvIPO1 vector was then transformed into *E. coli* BL21 (DE3) (Novagen, Darmstadt, Germany), for overexpression of the enzyme.

Briefly, a 3 ml overnight preculture of a transformed bacteria clone, pre-selected for its resistance to Ampicillin, was used to inoculate a 200 ml culture of the auto-inducible ZYP 5052 medium developed by Studier (2005) containing 200 μg/ml of Ampicillin. The recombinant bacteria were grown for 3 days at 20° C., and the cultured cells were pelleted by centrifugation (at 4000 g for 5 minutes) and frozen at −80° C. prior to purification.

The bacterial pellet was harvested by using of a French Press machine in presence of a lysis buffer (Tris-HCl pH8.8 50 mM). The lysate was then ultra-centrifuged for 1 h 30 min at 30,000 g prior to chromatography separation.

The resulting supernatant was collected and exchanged with buffer A (Tris-HCl pH7.5 50 mM; 200 mM NaCl; 100 mM KI; 50 mM imidazole) by dilution and transferred to a Ni-sepharose column. The extract was fractionated by IMAC affinity using an AKTA-purifier (Amersham). After a wash step with buffer A (Tris-HCl pH7.5 50 mM; 200 mM NaCl; 100 mM KI; 50 mM imidazole), the proteins were eluted using a gradient protocol of 50 mM to 500 mM imidazole by mixing buffer A and buffer B (Tris-HCl pH7.5 50 mM; 200 mM NaCl; 100 mM KI; 500 mM imidazole).

A gel electrophoresis of the eluted proteic fractions was carried out using 9% polyacrylamide slab gels according to Laemmli (1970). SDS-samples, containing β-mercaptoethanol, were boiled at 100° C. for 10 min to denature the proteins. The protein samples were then electrophoresed along with a protein molecular mass standard (Precision Plus Protein™ Standards, Bio-Rad Laboratories, Marnes La Coquette, France) and the resulting gel was stained with Coomassie brilliant blue R-250 to reveal the presence of the proteins.

The fractions of interest were then concentrated to a volume of 500 μl by ultrafiltration on a CentriPrep Centrifugal Filter Unit 10 kDa (Millipore) and simultaneously exchanged with a Tris-HCl pH7.5 50 mM buffer. The proteins were then transferred on Superdex 200 16/60 Prep Grade resin (Amersham) and purified by size chromatography using an ÄKTA-purifier (Amersham). Gel electrophoresis and Coomassie Blue staining were performed again to check for the presence of the recombinant protein in the eluted fractions (~50 kDa) and evaluate the purity of the enzyme in the protein samples.

I.4. Haloperoxidase Activity of the Purified ZgvIPO1

Haloperoxidase activities were detected on non-denaturing electrophoresis gels, soaked with 100 mM potassium phosphate buffer, pH 7.4, in the presence of 0.1 mM o-dianisidine, 0.45 mM H2O2, and 10 mM potassium iodide, potassium bromide, or potassium chloride in order to reveal iodoperoxidase, bromoperoxidase or chloroperoxidase activities, respectively (Jordan and Vilter, 1990).

To detect haloperoxidase activity on denaturating electrophoresis gels, the SDS was removed by washing the above gel 4 times in Tris-glycine buffer containing 0.1% Igepal CA-630 (Sigma Aldrich).

Such method allows identifying the specific enzymatic activity of the purified recombinant ZgvIPO1.

I.5. Enzymatic Kinetics Parameters of the Recombinant ZgvIPO1

A spectrophotometric assay to measure the iodoperoxidase activity of the recombinant ZgvIPO1 was carried out, according to the protocol based on the iodination of thymol blue described by Verhaeghe et al. (Anal. Biochem., 2008, 379: 60-65).

All reactions were performed in quadruplicate at 20° C. in a 1 mL standard assay. The stock solution of thymol blue (TB) was prepared in H2O/dimethylsulfoxide (DMSO) (4:1).

The assays were carried out as follows: 10 μg of the purified ZgvIPO1 enzyme were added to a reaction mixture, consisting of phosphate buffer (100 mM, pH 7.2), TB (100 μM), NaI (62.5 μM to 2 mM) and H2O2 (0.35 mM final). The iodoperoxidase activity was evaluated by measuring the absorbance of the resulting mixture at 620 nm on a Spectrophotometer UV-2401PC (Shimadzu) for 5 min. A620 values were then converted to millimolars of diiodothymolsulfonphthalein (TBI2) using the equation [C]=A620/40.3 mM-1 cm-1.

For the determination of kinetic parameters (Km and kcat values of iodide), the experimental initial velocities expressed in millimolars of iodine-converted per minute, were averaged and fitted to the Michaelis-Menten equation.

For thermostability studies, the purified recombinant proteins were maintained at the appropriate temperature for 10 min prior to the iodoperoxidase assay.

I.6. Crystallization of the ZgvIPO1 Enzyme

For crystallisation set up and 3D structure resolution, the Se-Met labelling procedure was performed by growing recombinant pFO4-ZgvIPO1 *E. coli* BL21 (DE3) in 200 ml of PASM 5052 medium (Studier, 2005) containing 200 μg/ml of Ampicillin at 20° C. during 10 days. The purification procedure was the same as for the native enzyme.

The over-expression and purification of the recombinant native and Se-Met-labelled ZgvIPO1 enzymes were carried out in sufficient quantity to set up conditions for the protein crystallization.

Single crystals of native and Se-Met-labelled ZgvIPO1 were obtained using hanging drop vapour diffusion method. High quality crystals were grown by mixing 1 μL of protein with 0.5 μl reservoir solution, containing 23% (w/v) PEG 1150, 100 mM phosphate/citrate buffer pH4.2, and 2% (v/v) glycerol.

The diffraction data sets and the refinement statistics of the ZgvIPO1 crystal structure are listed in Tables 2 and 3, respectively.

TABLE 2

Data collection statistics for the MAD data set of ZgvIPO1 (Beamline: ESRF ID23- EH1).

|  | Peak | Inflexion point | Remote |
|---|---|---|---|
| Wavelength (Å) | 0.9793 | 0.9796 | 0.9685 |
| Space group | | $P2_12_12_1$ | |
| Unit cell (Å) | a = 42.84 Å; b = 84.36 Å; c = 117.38 Å | | |
| | $\alpha = \beta = \gamma = 90°$ | | |
| Resolution (Å) | 20-1.80 | 20-1.80 | 20-1.90 |
| High resolution shell | 1.85-1.80 | 1.85-1.80 | 1.95-1.90 |
| No. of reflections[a] | 198076 (72492) | 198448 (74005) | 168928 (66137) |
| Completeness (%) | 99.1 (99.6) | 99.2 (99.7) | 99.1 (99.5) |
| Redundancy | 2.6 (2.6) | 2.6 (2.6) | 2.6 (2.6) |
| I/σI | 13.74 (5.17) | 10.91 (2.74) | 10.60 (2.52) |
| $R_{sym}$ | 5.3 (20.7) | 7.2 (44.2) | 8.3 (45.4) |

[a]Values in parentheses concern the high resolution shell.

TABLE 3

Refinement statistics for the crystal structure of ZgvIPO1.

| Refinement | |
|---|---|
| $R_{work}$ ($R_{free}$) | 16.3 (20.2) |
| R.m.s.d. bond lenths (Å) | 0.03 |
| R.m.s.d. bond angles (°) | 1.95 |
| Ramachandran plot | |
| Residues in most favored regions (%) | 97.01 |
| Residues in allowed regions (%) | 1.99 |
| Residues in disallowed regions (%) | 1 |
| Atom number (Factor B Mean (Å$^2$)) | |
| Protein | 3224 (15.53) |
| Solvent | 235 (25.15) |
| Co-factor | 5 (15.08) |
| Ion | 1 (14.2) |

II. Results

II.1. Nucleotide and Protein Sequence of ZgvIPO1

The annotation of the ZgvIPO1 gene on the Z. galactanivorans genome revealed a 1353 bp sequence (SEQ ID No 12), coding for a protein sequence of 450 amino-acids (SEQ ID No 3). The signal peptide was predicted using SIGNALP v.2.0 using both Neural Networks and Hidden Markov models (Nielsen et al., 1999) and was identified as the sequence MKKILIALISFAFAVSCKAPQK (SEQ ID No 6).

The nucleotide sequence of ZgvIPO1, minus the first 51 nucleotides of the 5' end of the sequence coding for the above putative signal peptide, was subsequently cloned in the expression vector pFO4 for production and characterization of the enzyme. The resulting cloned sequence is of sequence SEQ ID No 10 and comprises the stop codon TAA in the 3' extremity of said sequence, and codes for the amino-acid sequence SEQ ID No 1. The pFO4 vector carries a Histidine Tag of sequence SEQ ID No 9 in the 5' extremity of sequence SEQ ID No 10 for affinity purification of the protein, without the complete putative signal peptide sequence of the native protein.

II.2. Overexpression in E. coli and Purification of ZgvIPO1

Following overexpression and purification of ZgvIPO1 in E. coli, a recombinant protein with the expected size of about 50 kDa was produced, as shown by the gel electrophoresis stained with Coomassie blue of the purified eluted fractions (see FIG. 1). A contaminant protein of about 70 kDa was also present in the fractions 9 to 17. As a consequence, only the fractions 18 to 30, devoid of the other contaminant protein, were further concentrated and purified by size-exclusion chromatography (FIG. 2A).

Gel electrophoresis and Coomassie Blue staining revealed the presence of the recombinant protein ZgvIPO1 in the eluted fractions (~50 kDa) and that no contaminant protein was present (see FIG. 2B).

The high production yield was estimated to be of about 50 to 100 mg of recombinant protein per 1 L of microbial culture, and can thus support industrial scale production. The protein was fully soluble, and thus no refolding was necessary.

II.3. Haloperoxidase Activity of ZgvIPO1

The in gel activity assay, under non-denaturing conditions, revealed a strict iodoperoxidase activity of the ZgvIPO1 enzyme, as shown by FIG. 3 where major bands were detected only in the presence of iodide. Neither chloroperoxidase nor bromoperodixase activities were detected.

II.4. Enzymatic Kinetics Parameters of the Recombinant ZgvIPO1 Enzyme

The ZgvIPO1 specific activity showed typical Michaelis-Menten kinetics as function of iodide in the initial part of the curve, but started to decrease at 2 mM (FIG. 4A). The Lineweaver-Burke analysis at various fixed levels of iodide revealed a Km of 0.6 mM, and a Kcat of 36.5 s$^{-1}$ (FIG. 4B).

Upon heating for 10 min, the purified ZgvIPO1 remained fully active up to 40° C. (FIG. 5).

II.5. Crystallization Structure of the ZgvIPO1 Enzyme

The crystal structure of the first vIPO enzyme was solved using the multiple-wavelength anomalous dispersion (MAD) method employing Se-Metlabelled protein crystals and refined using data extending to a resolution of 1.8 Å (Table 2). Details of the final refinement statistics are listed in Table 3.

The global monomeric structure of ZgvIPO1 is folded into 14 α-helices and 2 310 helices with two short β-strands (FIG. 6). The main tertiary structural motif of two five-helix bundles is closer to the reported X-ray crystal structure of the vCPO from a terrestrial fungi, *Curvularia inaequalis* (Messerschmidt and Wever 1996).

REFERENCES

Vilter, H. (1995) in *Metal ions in biological systems* (Sigel, H., and Sigel, A., eds) Vol. 31, pp. 325-362, Marcel Dekker, Inc., New York, Basel, Hong Kong.

Butler, A., Carter, J. N., and Simpson, M. T. (2001) in *Handbook on Metalloproteins* (Bertini, I., Sigel, A., and Sigel, H., eds), pp. 153-179, Marcel Dekker, Inc., New York, Basel.

Messerschmidt, A., and Wever, R. (1996) *Proceedings of the National Academy of Sciences of the U.S.* 93, 392-396.

Shimonishi, M., Kuwamoto, S., Inoue, H., Wever, R., Ohshiro, T., Izumi, Y., and Tanabe, T. (1998) *FEBS letters* 428, 105-110.

Ohshiro, T., Hemrika, W., Aibara, T., Wever, R., and Izumi, Y. (2002) *Phytochemistry* 60, 595-601.

Isupov, M. N., Dalby, A. R., Brindley, A. A., Izumi, Y., Tanabe, T., Murshudov, G. N., and Littlechild, J. A. (2000) *J. Mol. Biol.* 299, 1035-1049

Carter, J. N., Beatty, K. E., Simpson, M. T., and Butler, A. (2002) *Journal of Inorganic Biochemistry* 91, 59-69.

Vreeland, V., Ng, K. L., and Epstein, L. (1998) *Molecular Biology of the Cell* 9, 1043.

Weyand, M., Hecht, H., Kiess, M., Liaud, M., Vilter, H., and Schomburg, D. (1999). *J Mol Biol.* 293(3):595-611.

Colin, C., Leblanc, C., Michel, G., Wagner, E., Leize-Wagner, E., Van Dorsselaer, A. and Potin, P. (2005). *J. Biol. Inorg. Chem.* 10, 156-166.

Verhaeghe, E., Buisson, D., Zekri, E., Leblanc, C., Potin, P., and Ambroise, Y. (2008). *Anal Biochem.* 379(1):60-65.

Smith and Waterman (1981) *J. Theor. Biol.*, 91(2), 370-380.

Needleman and Wunsch (1972) *J. Mol. Biol.* 48(3), 443-453.

Pearson and Lipman (1988) *PNAS USA* 85(5), 2444-2448.

Altschul, S. F., Gish, W., Miller, W., Myers, E. W., and Lipman, D. J. (1990). *J Mol Biol*, 215(3), 403-410.

Sambrook et al. (2001). *Molecular Cloning: A Laboratory Manual*, Cold Spring Harbor Laboratory Press; 3rd edition.

Ausubel et al. (2011). *Current Protocols in Molecular Biology*, John Wiley & Sons.

O'Reilly, D. R. et al. (1993). *"Baculovirus Expression Vectors: A Laboratory Manual"*, Oxford University Press, USA.

La Barre, S., Potin, P., Leblanc, C., and Delage L. (2010). *Mar. Drugs* 8(4), 988-1010.

Barbeyron, T., L'Haridon, S., Corre, E., Kloareg, B., and Potin, P. (2001). *Int J Syst Evol Microbiol.*, 51(Pt 3):985-97.

ZoBell, C. (1941). *J. Mar. Res.* 4:42-75.

Altschul, S. F., Madden, T. L., Schaffer, A. A., Zhang, J., Zhang, Z., Miller, W., and Lipman, D. J. (1997). *Nucleic Acids Res.*, 25: 3389-3402.

Groisillier, A Herve, C., Jeudy, A., Rebuffet, E., Pluchon, P. F., Chevolot, Y., Flament, D., Geslin, C., Morgado, I. M., Power, D., Branno, M., Moreau, H., Michel, G., Boyen, C. and Czjzek, M. (2010). *Cell Factories*, 9:45.

Studier (2005). *Protein Expr Purif*, 41:207-234.

Jordan P. and Vilter H. (1990). *Electrophoresis*, 11(8): 653-655.

Nielsen, H., Brunak, S., and von Heijne, G. (1999). *Protein Eng.*, 12: 3-9.

---

The invention claimed is:

1. A nucleic acid encoding an iodoperoxidase, wherein said nucleic acid comprises:
   SEQ ID NO:13 or SEQ ID NO:14, or
   a functional variant thereof having at least 95% sequence identity to SEQ ID NO:13 or SEQ ID NO:14.

2. A recombinant vector comprising a nucleic acid encoding a iodoperoxidase wherein said nucleic acid comprises:
   SEQ ID NO:10, SEQ ID NO:11, SEQ ID NO:12, SEQ ID NO:13 or SEQ ID NO:14, or
   a functional variant thereof having at least 95% sequence identity to SEQ ID NO:10, SEQ ID NO:11, SEQ ID NO:12, SEQ ID NO:13 or SEQ ID NO:14.

3. The recombinant vector according to claim 2, wherein said vector is a cloning vector or an expressing vector.

4. A recombinant host cell comprising a recombinant vector according to claim 2.

5. The recombinant host cell according to claim 4, wherein said cell is a prokaryotic cell or a eukaryotic cell.

6. A method for obtaining a iodoperoxidase, comprising at least the steps of:
   a) cloning into a recombinant expression vector a nucleic acid encoding a iodoperoxidase wherein said nucleic acid comprises:
      SEQ ID NO:10, SEQ ID NO:11, SEQ ID NO:12, SEQ ID NO:13 or SEQ ID NO:14, or
      a functional variant thereof having at least 95% sequence identity to SEQ ID NO:10, SEQ ID NO:11, SEQ ID NO:12, SEQ ID NO:13 or SEQ ID NO:14;
   b) transforming a recombinant host cell with said recombinant expression vector;
   c) expressing said isolated nucleic acid from said recombinant host cell, so as to obtain said iodoperoxidase.

7. The method according to claim 6, wherein said method further comprises the step d) of purifying said iodoperoxidase.

* * * * *